(12) United States Patent
Cinbis et al.

(10) Patent No.: US 9,636,512 B2
(45) Date of Patent: May 2, 2017

(54) IMPLANTABLE CARDIOVERTER-DEFIBRILLATOR (ICD) SYSTEM HAVING MULTIPLE COMMON POLARITY EXTRAVASCULAR DEFIBRILLATION ELECTRODES

(71) Applicant: Medtronic, Inc., Minneapolis, MN (US)

(72) Inventors: Can Cinbis, Salt Lake City, UT (US); Vladimir P. Nikolski, Blaine, MN (US); Jian Cao, Shoreview, MN (US); James K. Carney, Roseville, MN (US); Melissa G. T. Christie, Ham Lake, MN (US); Richard J. O'Brien, Hugo, MN (US); Amy E. Thompson-Nauman, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/932,311

(22) Filed: Nov. 4, 2015

(65) Prior Publication Data

US 2016/0121130 A1  May 5, 2016

Related U.S. Application Data

(60) Provisional application No. 62/075,589, filed on Nov. 5, 2014, provisional application No. 62/075,312, filed on Nov. 5, 2014.

(51) Int. Cl.
*A61N 1/39* (2006.01)
*A61N 1/362* (2006.01)
*A61N 1/05* (2006.01)

(52) U.S. Cl.
CPC ......... *A61N 1/3962* (2013.01); *A61N 1/0587* (2013.01); *A61N 1/3621* (2013.01); *A61N 1/3987* (2013.01)

(58) Field of Classification Search
CPC .................................................. A61N 1/3918
See application file for complete search history.

(56) References Cited

U.S. PATENT DOCUMENTS 4,030,509 A  6/1977  Heilman et al.
4,146,037 A  3/1979  Flynn et al.
(Continued)

FOREIGN PATENT DOCUMENTS

EP  1541191 A1  6/2005
WO  2001023035 A1  4/2001
(Continued)

OTHER PUBLICATIONS

Obadia, et al., "New Approach for Implantation of Automatic Defibrillators Using Videothoracoscopy", Journal Ann Cardiol Angeiol (Paris); Sep. 1994; 43 (7) Abstract Only, 1 page.
(Continued)

*Primary Examiner* — Kennedy Schaetzle

(57) ABSTRACT

This disclosure provides an extravascular ICD system and method for defibrillating a heart of a patient. The extravascular ICD system includes multiple extravascular electrical stimulation leads or lead segments located in close proximity to one another and having respective defibrillation electrodes. The ICD system utilizes the multiple defibrillation electrodes to form an extravascular electrode vector that may result a reduction in the shock impedance and/or a reduction in the DFT compared to extravascular ICD systems that include only a single extravascular defibrillation electrode. An ICD of the system may, for example, deliver a defibrillation shock using an electrode vector in which a first polarity of the electrode vector is formed by electrically coupling first and second defibrillation electrodes of first and second leads, respectively, to the therapy circuitry and a second polarity of the electrode vector is formed by elec-
(Continued)

trically coupling a housing of the ICD to the therapy circuitry.

22 Claims, 12 Drawing Sheets

(56) References Cited

U.S. PATENT DOCUMENTS

| | | | |
|---|---|---|---|
| 4,270,549 A | 6/1981 | Heilman | |
| 4,280,510 A | 7/1981 | O'Neill | |
| 4,291,707 A | 9/1981 | Heilman et al. | |
| 4,437,475 A | 3/1984 | White | |
| 4,512,351 A | 4/1985 | Pohndorf | |
| 4,538,624 A | 9/1985 | Tarjan | |
| 4,628,934 A | 12/1986 | Pohndorf et al. | |
| 4,765,341 A | 8/1988 | Mower et al. | |
| 4,832,687 A | 5/1989 | Smith, III | |
| 4,998,975 A | 3/1991 | Cohen et al. | |
| 5,036,854 A | 8/1991 | Schollmeyer et al. | |
| 5,052,390 A * | 10/1991 | Hewson | A61N 1/0517 607/124 |
| 5,105,826 A | 4/1992 | Smits et al. | |
| 5,107,834 A | 4/1992 | Ideker et al. | |
| 5,125,904 A | 6/1992 | Lee | |
| 5,144,960 A | 9/1992 | Mehra et al. | |
| 5,174,288 A | 12/1992 | Bardy et al. | |
| 5,176,135 A | 1/1993 | Fain et al. | |
| 5,203,348 A | 4/1993 | Dahl et al. | |
| 5,255,691 A | 10/1993 | Otten | |
| 5,255,692 A | 10/1993 | Neubauer et al. | |
| 5,271,417 A | 12/1993 | Swanson et al. | |
| 5,273,053 A | 12/1993 | Pohndorf | |
| 5,282,845 A | 2/1994 | Bush et al. | |
| 5,300,106 A | 4/1994 | Dahl et al. | |
| 5,312,355 A | 5/1994 | Lee | |
| 5,325,870 A | 7/1994 | Kroll et al. | |
| 5,342,407 A | 8/1994 | Dahl et al. | |
| 5,360,442 A | 11/1994 | Dahl et al. | |
| 5,388,578 A | 2/1995 | Yomtov et al. | |
| 5,441,504 A | 8/1995 | Pohndorf et al. | |
| 5,456,699 A | 10/1995 | Armstrong | |
| 5,456,706 A | 10/1995 | Pless et al. | |
| 5,464,447 A * | 11/1995 | Fogarty | A61N 1/0587 600/374 |
| 5,476,493 A | 12/1995 | Muff | |
| 5,509,924 A | 4/1996 | Paspa et al. | |
| 5,534,018 A | 7/1996 | Wahlstrand et al. | |
| 5,571,074 A * | 11/1996 | Buckman, Jr. | A61M 1/1068 601/41 |
| 5,613,953 A | 3/1997 | Pohndorf | |
| 5,690,648 A | 11/1997 | Fogarty et al. | |
| 5,800,465 A | 9/1998 | Thompson et al. | |
| 5,944,732 A | 8/1999 | Raulerson et al. | |
| 5,951,518 A | 9/1999 | Licata et al. | |
| 6,006,131 A | 12/1999 | Cooper et al. | |
| 6,032,079 A | 2/2000 | KenKnight et al. | |
| 6,104,957 A | 8/2000 | Alo et al. | |
| 6,122,552 A | 9/2000 | Tockman et al. | |
| 6,159,198 A | 12/2000 | Gardeski et al. | |
| 6,228,052 B1 | 5/2001 | Pohndorf | |
| 6,295,475 B1 | 9/2001 | Morgan | |
| 6,324,414 B1 | 11/2001 | Gibbons et al. | |
| 6,415,187 B1 | 7/2002 | Kuzma et al. | |
| 6,445,954 B1 | 9/2002 | Olive et al. | |
| 6,473,653 B1 | 10/2002 | Schallhorn et al. | |
| 6,544,247 B1 | 4/2003 | Gardeski et al. | |
| 6,658,289 B2 | 12/2003 | Helland | |
| 6,721,597 B1 | 4/2004 | Bardy et al. | |
| 6,721,598 B1 | 4/2004 | Helland et al. | |
| 6,730,083 B2 | 5/2004 | Freigang et al. | |
| 6,733,500 B2 | 5/2004 | Kelley et al. | |
| 6,749,574 B2 | 6/2004 | O'Keefe | |
| 6,770,070 B1 | 8/2004 | Balbierz | |
| 6,772,014 B2 | 8/2004 | Coe et al. | |
| 6,836,687 B2 | 12/2004 | Kelley et al. | |
| 6,868,291 B1 | 3/2005 | Bonner et al. | |
| 6,887,229 B1 | 5/2005 | Kurth | |
| 6,890,295 B2 | 5/2005 | Michels et al. | |
| 6,952,610 B2 | 10/2005 | Ostroff et al. | |
| 6,978,178 B2 | 12/2005 | Sommer et al. | |
| 6,999,819 B2 | 2/2006 | Swoyer et al. | |
| 7,033,326 B1 | 4/2006 | Pianca et al. | |
| 7,050,851 B2 | 5/2006 | Plombon et al. | |
| 7,069,083 B2 | 6/2006 | Finch et al. | |
| 7,117,039 B2 | 10/2006 | Manning et al. | |
| 7,142,919 B2 | 11/2006 | Hine et al. | |
| 7,195,637 B2 | 3/2007 | Mika | |
| 7,218,970 B2 | 5/2007 | Ley et al. | |
| 7,225,034 B2 | 5/2007 | Ries et al. | |
| 7,229,450 B1 | 6/2007 | Chitre et al. | |
| 7,242,987 B2 | 7/2007 | Holleman et al. | |
| 7,272,448 B1 | 9/2007 | Morgan et al. | |
| 7,288,096 B2 | 10/2007 | Chin | |
| 7,316,667 B2 | 1/2008 | Lindstrom et al. | |
| 7,322,960 B2 | 1/2008 | Yamamoto et al. | |
| 7,369,899 B2 | 5/2008 | Malinowski et al. | |
| 7,389,134 B1 | 6/2008 | Karicherla et al. | |
| 7,418,293 B2 | 8/2008 | Sweeney | |
| 7,450,997 B1 | 11/2008 | Pianca et al. | |
| 7,499,758 B2 | 3/2009 | Cates et al. | |
| 7,539,542 B1 | 5/2009 | Malinowski | |
| 7,627,375 B2 | 12/2009 | Bardy et al. | |
| 7,655,014 B2 | 2/2010 | Ko et al. | |
| 7,736,330 B2 | 6/2010 | Bardy | |
| 7,761,150 B2 | 7/2010 | Ghanem et al. | |
| 7,765,014 B2 | 7/2010 | Eversull et al. | |
| 7,801,622 B2 | 9/2010 | Camps et al. | |
| 7,837,671 B2 | 11/2010 | Eversull et al. | |
| 7,846,088 B2 | 12/2010 | Ness | |
| 7,850,610 B2 | 12/2010 | Ferek-Petric | |
| 7,890,191 B2 | 2/2011 | Rutten et al. | |
| 7,908,015 B2 | 3/2011 | Lazeroms et al. | |
| 7,930,028 B2 | 4/2011 | Lang et al. | |
| 7,930,040 B1 | 4/2011 | Kelsch et al. | |
| 7,983,765 B1 | 7/2011 | Doan et al. | |
| 8,060,207 B2 | 11/2011 | Wallace et al. | |
| 8,065,020 B2 | 11/2011 | Ley et al. | |
| 8,066,702 B2 | 11/2011 | Rittman, III et al. | |
| 8,090,451 B2 | 1/2012 | Tyson, Jr. | |
| 8,155,755 B2 | 4/2012 | Flynn et al. | |
| 8,157,813 B2 | 4/2012 | Ko et al. | |
| 8,260,436 B2 | 9/2012 | Gerber et al. | |
| 8,280,527 B2 | 10/2012 | Eckerdal et al. | |
| 8,340,779 B2 | 12/2012 | Harris et al. | |
| 8,355,786 B2 | 1/2013 | Malinowski | |
| 8,386,037 B2 | 2/2013 | Ostroff et al. | |
| 8,386,052 B2 | 2/2013 | Harris et al. | |
| 8,394,079 B2 | 3/2013 | Drake et al. | |
| 8,435,208 B2 | 5/2013 | Bardy | |
| 8,442,620 B2 | 5/2013 | Silipo et al. | |
| 8,452,421 B2 | 5/2013 | Thenuwara et al. | |
| 8,478,424 B2 | 7/2013 | Tronnes | |
| 8,478,426 B2 | 7/2013 | Barker | |
| 8,594,809 B2 | 11/2013 | Yang et al. | |
| 8,886,311 B2 | 11/2014 | Anderson et al. | |
| 9,511,233 B2 * | 12/2016 | Sambelashvili | A61N 1/3688 |
| 2002/0035377 A1 * | 3/2002 | Bardy | A61N 1/375 607/4 |
| 2002/0120294 A1 | 8/2002 | Kroll | |
| 2003/0088278 A1 | 5/2003 | Bardy et al. | |
| 2003/0114908 A1 | 6/2003 | Flach | |
| 2004/0059348 A1 | 3/2004 | Geske et al. | |
| 2004/0102829 A1 | 5/2004 | Bonner et al. | |
| 2004/0143284 A1 * | 7/2004 | Chin | A61B 17/3468 606/192 |
| 2004/0210293 A1 | 10/2004 | Bardy et al. | |
| 2004/0215240 A1 | 10/2004 | Lovett et al. | |
| 2004/0230279 A1 | 11/2004 | Cates et al. | |
| 2004/0230280 A1 | 11/2004 | Cates et al. | |
| 2004/0230281 A1 | 11/2004 | Heil et al. | |
| 2004/0230282 A1 | 11/2004 | Cates et al. | |
| 2004/0236396 A1 | 11/2004 | Coe et al. | |
| 2004/0267328 A1 | 12/2004 | Duffin et al. | |

(56) References Cited

U.S. PATENT DOCUMENTS

| | | |
|---|---|---|
| 2005/0049663 A1 | 3/2005 | Harris et al. |
| 2005/0055056 A1* | 3/2005 | Olson .................. A61N 1/3622 607/5 |
| 2005/0131505 A1 | 6/2005 | Yokoyama |
| 2005/0277990 A1 | 12/2005 | Ostroff et al. |
| 2005/0288758 A1 | 12/2005 | Jones et al. |
| 2006/0041295 A1 | 2/2006 | Okypka |
| 2006/0116746 A1 | 6/2006 | Chin |
| 2006/0122676 A1 | 6/2006 | Ko et al. |
| 2006/0136004 A1 | 6/2006 | Cowan et al. |
| 2006/0161205 A1 | 7/2006 | Mitrani et al. |
| 2006/0247753 A1 | 11/2006 | Wenger et al. |
| 2006/0253181 A1 | 11/2006 | Schulman et al. |
| 2007/0023947 A1 | 2/2007 | Ludwig et al. |
| 2007/0049975 A1* | 3/2007 | Cates ..................... A61N 1/375 607/5 |
| 2007/0088394 A1 | 4/2007 | Jacobson |
| 2007/0100409 A1 | 5/2007 | Worley et al. |
| 2007/0135847 A1* | 6/2007 | Kenknight ............... A61N 1/05 607/5 |
| 2007/0179388 A1 | 8/2007 | Larik et al. |
| 2007/0208402 A1 | 9/2007 | Helland et al. |
| 2007/0249992 A1 | 10/2007 | Bardy |
| 2008/0046056 A1 | 2/2008 | O'Connor |
| 2008/0243219 A1 | 10/2008 | Malinowski et al. |
| 2008/0269716 A1 | 10/2008 | Bonde et al. |
| 2009/0157091 A1 | 6/2009 | Buysman |
| 2009/0222021 A1 | 9/2009 | Chang |
| 2009/0259283 A1 | 10/2009 | Brandt et al. |
| 2009/0264780 A1 | 10/2009 | Schilling |
| 2009/0270962 A1 | 10/2009 | Yang et al. |
| 2010/0016935 A1 | 1/2010 | Strandberg et al. |
| 2010/0030227 A1 | 2/2010 | Kast et al. |
| 2010/0030228 A1 | 2/2010 | Havel |
| 2010/0056858 A1 | 3/2010 | Mokelke et al. |
| 2010/0094252 A1 | 4/2010 | Wengreen et al. |
| 2010/0113963 A1 | 5/2010 | Smits et al. |
| 2010/0125194 A1 | 5/2010 | Bonner et al. |
| 2010/0137879 A1 | 6/2010 | Ko et al. |
| 2010/0152747 A1 | 6/2010 | Padiy et al. |
| 2010/0152798 A1* | 6/2010 | Sanghera ............. A61N 1/0504 607/5 |
| 2010/0211064 A1 | 8/2010 | Mahapatra et al. |
| 2010/0217298 A1 | 8/2010 | Bardy |
| 2010/0217301 A1 | 8/2010 | Bardy |
| 2010/0241185 A1 | 9/2010 | Mahapatra et al. |
| 2010/0249696 A1 | 9/2010 | Bardy |
| 2010/0305428 A1 | 12/2010 | Bonner et al. |
| 2010/0318098 A1 | 12/2010 | Lund et al. |
| 2011/0009933 A1 | 1/2011 | Barker |
| 2011/0077708 A1 | 3/2011 | Ostroff |
| 2011/0125163 A1 | 5/2011 | Rutten et al. |
| 2011/0224680 A1 | 9/2011 | Barker |
| 2011/0224681 A1 | 9/2011 | McDonald |
| 2011/0257660 A1 | 10/2011 | Jones et al. |
| 2012/0016377 A1 | 1/2012 | Geroy |
| 2012/0029335 A1 | 2/2012 | Sudam et al. |
| 2012/0078266 A1 | 3/2012 | Tyson, Jr. |
| 2012/0089153 A1 | 4/2012 | Christopherson et al. |
| 2012/0097174 A1 | 4/2012 | Spotnitz et al. |
| 2012/0123496 A1 | 5/2012 | Schotzko et al. |
| 2012/0191106 A1 | 7/2012 | Ko et al. |
| 2012/0209283 A1 | 8/2012 | Zhu |
| 2012/0209285 A1 | 8/2012 | Barker et al. |
| 2012/0316613 A1 | 12/2012 | Keefe et al. |
| 2013/0041345 A1 | 2/2013 | Kilcoin et al. |
| 2013/0103049 A1 | 4/2013 | Bonde |
| 2013/0158564 A1 | 6/2013 | Harris et al. |
| 2013/0238067 A1 | 9/2013 | Baudino |
| 2014/0039238 A1* | 2/2014 | Min ..................... A61B 5/0215 600/9 |
| 2015/0306408 A1* | 10/2015 | Greenhut ............... A61B 5/686 607/5 |
| 2015/0306410 A1 | 10/2015 | Marshall et al. |
| 2016/0106991 A1* | 4/2016 | Stadler .................. A61N 1/3987 607/5 |

FOREIGN PATENT DOCUMENTS

| | | |
|---|---|---|
| WO | 2004073506 A2 | 9/2004 |
| WO | 2010047893 A1 | 4/2010 |

OTHER PUBLICATIONS

Lemmer, "Defibrillator Patch Constriction, Letter to the Editor", The Annals of Thoracic Surgery, 1996, 1 page.

Ely et al., "Thoracoscopic Implantation of the Implantable Cardioverter Defibrillator", Minimally Invasive Techniques; (Can be found on the World-Wide Web at http://chestioumal.chestpubs.org on May 6, 2013); dated Jan. 1993; 2 pages.

Damiano, "Implantation of Cardioverter Defibrillators in the Post-Sternotomy Patient", The Annals of Thoracic Surgery, 1992; 53: pp. 978-983.

Piccione, et al., "Erosion of Extrapericardial Implantable Cardioverter Defibrillator Patch Through the Gastic Fundus with Fistulous Tract Information", Cardiology in Review; 2006; 14, e21-e23 pages.

Vyhmeister et al., "Simple Approach for Extrapericardial Placement of Defibrillator Patches via Median Sternotomy", The Annals of Thoracic Surgery; 1994; 57: 4 pages.

Harman et al., "Differences in the Pathological Changes in Dogs' Hearts After Defibrillation with Extrapericardial Paddles and Implanted Defibrillator Electrodes", Journal of Pacing and Clinical Electrophysiology, Feb. 1991; vol. 14; Part 2; 5 pages.

Obadia et al., "Thoracoscopic Approach to Implantable Cardioverter Defibrillator Patch Electrode Implantation", Pacing and Clinical Electrophysiology; Jun. 1996; vol. 19; 6 pages.

Shapira, et al., "A Simplied Method for Implantation of Automatic Cardioverter Defibrillator in Patients with Previous Cardiac Surgery", Pacing and Clinical Electrophysiology, Jan. Part I, 1993, vol. 16; 6 pages.

Quigley et al., "Migration of an Automatic Implantable Cardioverter-Defibrillator Patch Causing Massive Hemothorax", Journal Texas Heart Institute, Nov. 1, 1996; vol. 23, 4 pages.

Karwande et al., "Bilateral Anterior Thoracotomy for Automatic Implantable Cardioverter Defibrillator Placement in Patients with Previous Sternotomy", The Annals of Thoracic Surgery; Oct. 1992; 54(4); 3 pages.

Bielefeld et al., "Thoracoscopic Placement of Implantable Cardioverter-Defibrillator Patch Leads in Sheep", Circulation; Nov. 1993, vol. 88, No. 5, Part 2; 5 pages.

Frame et al., "Long-Term Stability of Defibrillation Thresholds with Intrapericardial Defibrillator Patches", Pacing and Clinical Electrophysiology, Jan. 1993, Part II, vol. 16, 6 pages.

Lawrie et al., "Right Mini-Thoracotomy: An Adjunct to Left Subcostal Automatic Implantable Cardioverter Defibrillator Implantation", The Annals of Thoracic Surgery; 1989; 47; 4 pages.

Mitchell et al., "Experience with an Implantable Tiered Therapy Device Incorporating Antitachycardia Pacing and Cardioverter/Defibrillator Therapy", Thoracic and Cardiovascular Surgery, Abstract Only, Mar. 1993, 1 page.

Bolling et al., "Automatic Internal Cardioverter Defibrillator: A Bridge to Heart Transplantation", Heart Lung Transplantation, Abstract Only, Jul.-Aug. 1991, 1 page.

Steinke et al., "Subepicardial Infarction, Myocardial Impression, and Ventricular Penetration by Sutureless Electrode and Leads", Chest; 70: 1, Jul. 1976, 2 pages.

Avogadros Lab Supply Inc., Catalog; Scoopula with Beech Wood Handle, can be found on-line at http://www.avogadro-lab-supply.com/search.php, accessed Oct. 6, 2013, 1 page.

Medtronic, Inc. 6996SQ Subcutaneous, Unipolar Lead with Defibrillation Coil Electrode, Technical Manual, 22 pages.

Medtronic, Inc. 6996T Tunneling Tool, Technical Manual, 12 pages.

(56) References Cited

OTHER PUBLICATIONS

Pebax Product Brochure, 14 pages and can be found on-line at http://www.pebax.com/export/sites/pebax/.content/medias/downloads/literature/pebax-product-range-brochure.pdf, 14 pages.
Cigna et al., "A New Technique for Substernal Colon Transposition with a Breast Dissector: Report of 39 Cases", Journal of Plastic, Reconstructive and Aesthetic Surgery, 2006:59, 4 pages.
Tung et al., "Minimal Invasive Extra Cardiac Placement of High Voltage Defibrillator Leads", Poster 3; S200 Abstract, PO-3-4; St. Paul Hospital, Vancouver, British Columbia, Canada, 1 pages.
Molina et al, "An Epicardial Subxiphoid Implantable Defibrillator Lead: Superior Effectiveness After Failure of Standard Implants", From the Department of Surgery, Division of Cardiovascular and Thoracic Surgery and the Department of Medicine, Cardiac Arrhymthmia Center, University of Minnesota Medical School, Minneapolis, Minnesota, Pace, vol. 27, Nov. 2004, 7 pages.
Baudoin et al., "The Superior Epigastric Artery Does Not Pass Through Larrey's Space (Trigonum Sternocostale)", Surgical Radiol Anat (2003), 25: 259-262.
Haydin et al., "Subxiphoid Approach to Epicardial Implantation of Implantable Cardioverter Defibrillators in Children", PACE, vol. 36, Aug. 2013, 5 pages.

Falk et al., "External Cardiac Pacing Using Low Impedance Electrodes Suitable for Defibrillation: A Comparative Blinded Study," Journal of American College of Cardiology, vol. 22, No. 5, Nov. 1, 1993, 5 pages.
Laudon, M. K., "Pulse Output", Chapter 11 of Design of Pacemakers, Published by the Institute of Electrical and Electronics Engineers, Inc., New York,(1995), 30 pages.
Ganapathy et al., "Implantable Device to Monitor Cardiac Activity with Sternal Wires," Pace, vol. 37, Dec. 2014, 11 pages.
Guenther et al., "Substernal Lead Implantation: A Novel Option to Manage DFT Failure in S-ICD patients," Clinical Research Cardiology, Published On-line Oct. 2, 2014, 3 pages.
Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.com/ccc2007/abs/0697.htm, 2 pages.
Wetherbee et al., "Nonthoracotomy Internal Defibrillation in Dogs: Threshold Reduction Using a Subcutaneous Chest Wall Electrode with a Transvenous Catheter Electrode," Journal of the American College of Cardiology, vol. 10, No. 2, Aug. 1987, 6 pages.

\* cited by examiner

IMPLANTABLE CARDIOVERTER-DEFIBRILLATOR (ICD) SYSTEM HAVING MULTIPLE COMMON POLARITY EXTRAVASCULAR DEFIBRILLATION ELECTRODES

TECHNICAL FIELD

The present application relates to methods, systems and devices for providing an implantable cardiac defibrillation system having multiple common polarity extravascular defibrillation leads.

BACKGROUND

Malignant tachyarrhythmia, for example, ventricular fibrillation, is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients at high risk of ventricular fibrillation, the use of an implantable cardioverter-defibrillator (ICD) system has been shown to be beneficial at preventing SCD. Conventional ICD systems include an ICD that is coupled to one or more electrical stimulation leads placed on or within the heart. If a malignant tachyarrhythmia is sensed, the ICD delivers a cardioversion/defibrillation shock via a defibrillation electrode of the electrical lead to restore the heart to its normal rhythm. Owing to the inherent surgical risks in attaching and replacing electrical leads directly within or on the heart, subcutaneous ICD systems have been devised to provide cardioversion or defibrillation shocks to the heart using an electrical stimulation lead implanted subcutaneously outside the torso of the patient (e.g., outside of the ribcage).

Subcutaneous ICD systems may require an output of around 75-80 Joules (J) of energy to provide effective defibrillation therapy. As a result, subcutaneous ICDs may require larger batteries and more storage capacitors than transvenous ICDs. As such, the subcutaneous ICDs are generally larger in size than transvenous ICDs. The large size of the subcutaneous ICD may compromise patient comfort, decrease system longevity and/or increase cost of the system. In addition, subcutaneous ICD systems are incapable of delivering anti-tachycardia pacing (ATP), which is a standard therapy in transvenous ICDs to terminate ventricular tachyarrhythmias without providing a cardioversion or defibrillation shock.

SUMMARY

In general, this disclosure is related to an ICD system having multiple extravascular electrical stimulation leads having respective defibrillation electrodes, and located in close proximity to one another, are utilized to form an electrode vector that may result a reduction in the shock impedance and/or a reduction in the defibrillation threshold (DFT) compared to extravascular ICD systems that include only a single extravascular defibrillation electrode. An ICD of the system may, for example, deliver a defibrillation shock using an electrode vector in which a first polarity of the electrode vector is formed by electrically coupling a first and second defibrillation electrode of a first and second lead, respectively, to the therapy circuitry and a second polarity of the electrode vector is formed by electrically coupling a housing of the ICD to the therapy circuitry.

In one example, this disclosure provides an implantable cardioverter-defibrillator (ICD) system comprising an ICD implanted extra-thoracically in a patient and a first and second electrical stimulation lead. The ICD includes a housing, a power source within the housing, a therapy module within the housing that includes at least one defibrillation capacitor, and a control module within the housing. The first electrical stimulation lead has a proximal portion coupled to the ICD and a distal portion having a first defibrillation electrode configured to deliver a defibrillation shock from a substernal location to a heart of the patient. The first electrode is implanted at least partially along a posterior side of a sternum of the patient in the substernal location. The second electrical stimulation lead has a proximal portion coupled to the ICD and a distal portion having a second defibrillation electrode configured to deliver a defibrillation shock to the heart of the patient. The control module is configured to couple the at least one defibrillation capacitor to an electrode vector to deliver a high voltage shock to the heart of the patient. The control module couples the at least one defibrillation capacitor to the first and second defibrillation electrodes concurrently to form a first polarity of the electrode vector and to the housing of the ICD to form a second polarity of the electrical vector.

In another instance, this disclosure provides a method for extravascularly defibrillating a heart of a patient. The method includes obtaining electrical signals sensed from a substernal location via one or more electrodes in the substernal location; processing the electrical signals to detect a tachyarrhythmia; charging one or more defibrillation capacitors in response to detecting the tachyarrhythmia; electrically coupling the one or more defibrillation capacitors to an electrode vector to deliver a defibrillation therapy to the heart of the patient, the electrode vector including a first polarity formed by a first defibrillation electrode of a first electrical stimulation lead and a second defibrillation electrode of a second electrical stimulation lead and a second polarity formed by a housing of an implantable cardioverter-defibrillator (ICD), wherein the first defibrillation electrode is implanted at least partially in the substernal location.

In a further example, an implantable cardioverter-defibrillator (ICD) system comprises an ICD implanted in a patient under the skin and outside of the ribcage and an electrical stimulation lead having a lead body that includes a proximal portion configured to be coupled to the ICD and a distal portion. The ICD includes a housing, a power source within the housing, a therapy module within the housing that includes at least one defibrillation capacitor, and a control module within the housing. The distal portion of the electrical stimulation lead includes a first lead segment having a first defibrillation electrode configured to deliver a defibrillation shock from a substernal location to a heart of the patient and second lead segment having a second defibrillation electrode configured to deliver a defibrillation shock to the heart of the patient. The control module is configured to couple the at least one defibrillation capacitor to an electrode vector to deliver a high voltage shock to the heart of the patient, wherein the control module couples the at least one defibrillation capacitor to the first and second defibrillation electrodes concurrently to form a first polarity of the electrode vector and to the housing of the ICD to form a second polarity of the electrical vector.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
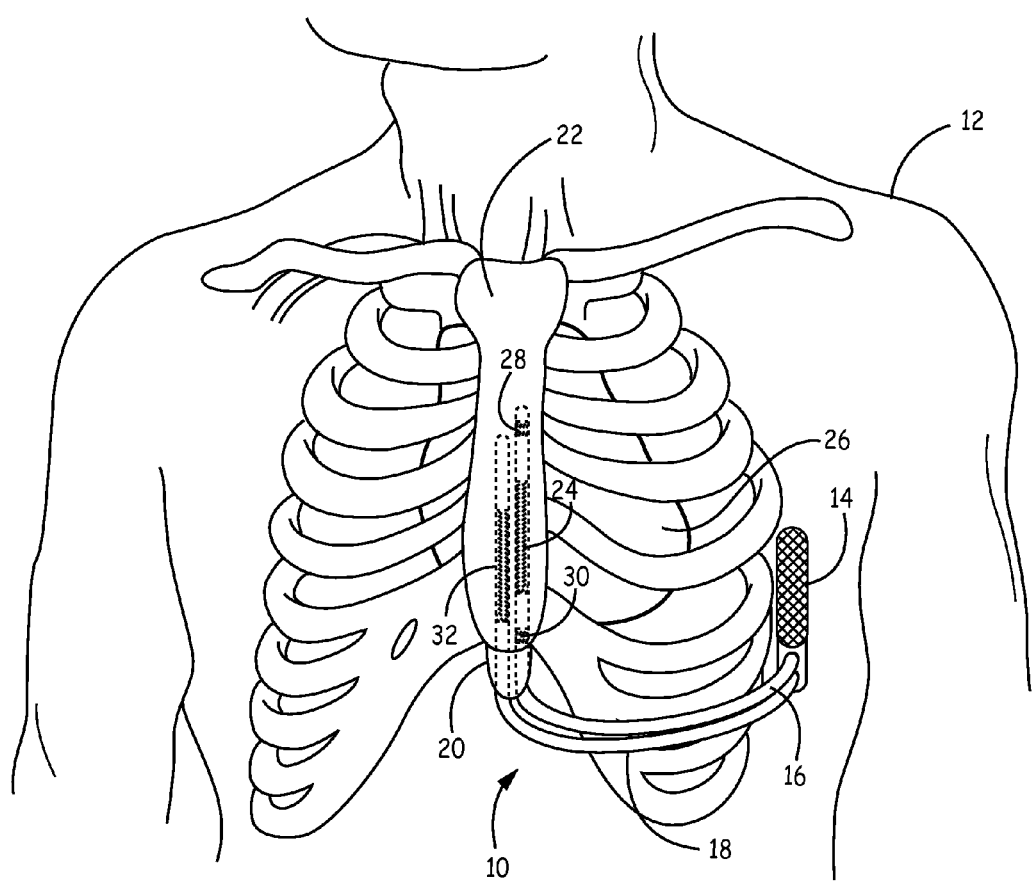
FIGS. 1A and 1B are conceptual diagrams of an extravascular implantable cardiac defibrillation system having two electrical stimulation leads, each with a respective defibrillation electrode, implanted within a substernal location of the patient.
Figure 1B:
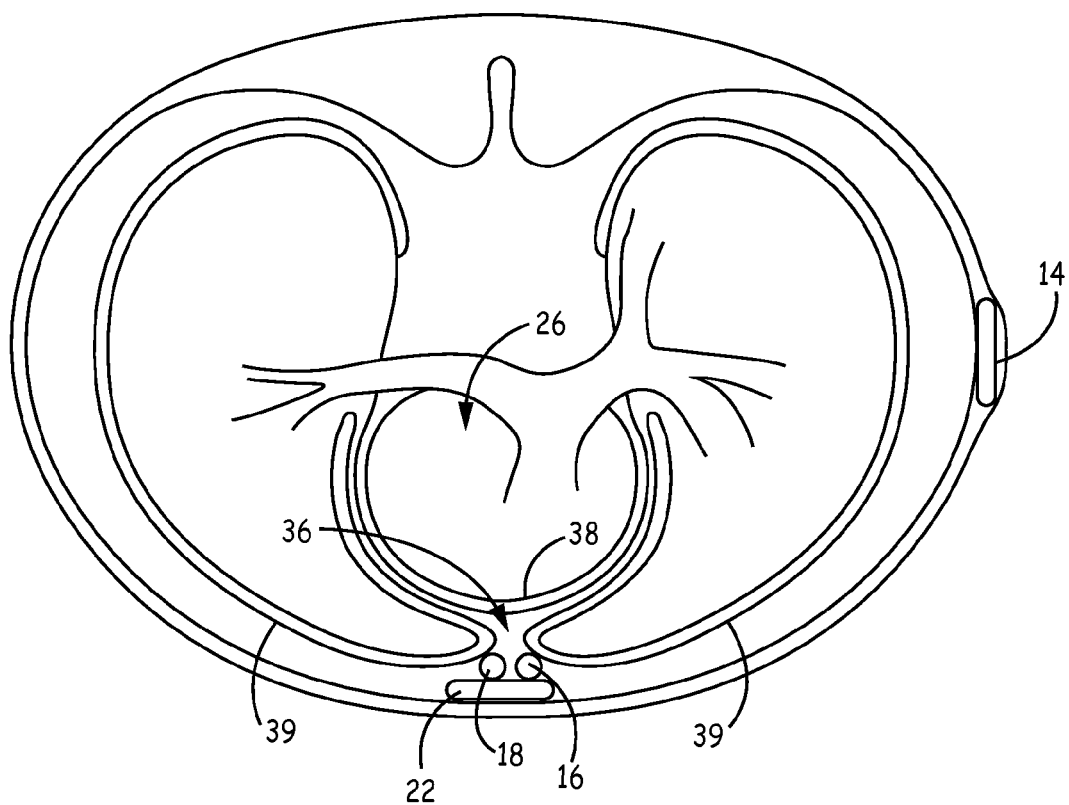

FIGS. 1A and 1B are conceptual diagrams of an extravascular implantable cardiac defibrillation system, e.g., extravascular ICD system 10, implanted within a patient 12. ICD system 10 includes an ICD 14 connected to electrical stimulation leads 16 and 18. FIG. 1A is a front view of patient 12 implanted with ICD system 10. FIG. 1B is a transverse view of patient 12 implanted with ICD system 10.

ICD 14 may include a housing that forms a hermetic seal that protects components of ICD 14. The housing of ICD 14 may be formed of a conductive material, such as titanium or titanium alloy, which may function as a housing electrode (sometimes referred to as a can electrode). In other embodiments, ICD 14 may be formed to have or may include one or more electrodes on the outermost portion of the housing. ICD 14 may also include a connector assembly (also referred to as a connector block or header) that includes electrical feedthroughs through which electrical connections are made between conductors of leads 16 and 18 and electronic components included within the housing of ICD 14. As will be described in further detail herein, housing may house one or more processors, memories, transmitters, receivers, sensors, sensing circuitry, therapy circuitry, power sources and other appropriate components. The housing is configured to be implanted in a patient, such as patient 12.

ICD 14 is implanted extra-thoracically on the left side of patient 12, e.g., under the skin and outside the ribcage and sternum (subcutaneously or submuscularly). ICD 14 may, in some instances, be implanted between the left posterior axillary line and the left anterior axillary line of patient 12. ICD 14 may, however, be implanted at other extra-thoracic locations on patient 12 as described later.

Lead 16 includes an elongated lead body having a proximal end that includes a connector (not shown in FIGS. 1A and 1B) configured to connect to ICD 14 and a distal portion that includes electrodes 24, 28 and 30. Lead 18 also includes an elongated lead body having a proximal end that includes a connector configured to connect to ICD 14 and a distal portion that includes an electrode 32. The connector may, for example, be a DF-1 or DF-4 type connector.

Leads 16 and 18 extend extra-thoracically from ICD 14 toward a center of the torso of patient 12, e.g., toward the xiphoid process of patient 12. At a location near the center of the torso, leads 16 and 18 bend or turn and extend superior in a substernal location under the sternum 22 and/or ribcage of patient 12 (intra-thoracically). In one example, the substernal location is substantially within an anterior mediastinum 36 such that distal portion of leads 16 and 18 extends superior along the posterior side of the sternum within anterior mediastinum 36. Anterior mediastinum 36 may be viewed as being bounded laterally by pleurae 39, posteriorly by pericardium 38, and anteriorly by the sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), the thymus gland, branches of the internal thoracic artery, and the internal thoracic vein. In one example, the distal portion of leads 16 and 18 may be implanted substantially within the loose connective tissue and/or substernal musculature of anterior mediastinum 36. A lead having a distal portion implanted substantially within anterior mediastinum 36 will be referred to herein as a substernal lead. Also, electrical stimulation, such as pacing, cardioversion or defibrillation, provided by ICD 14 from the substernal location via leads 16 and 18 will be referred to herein as substernal electrical stimulation, substernal pacing, substernal cardioversion, and/or substernal defibrillation.

The distal portion of leads 16 and 18 is described with respect to FIGS. 1A and 1B as being implanted substantially within anterior mediastinum 36. In other embodiments, the distal portion of leads 16 and 18 may be implanted in other non-vascular, extra-pericardial, intra-thoracic locations, including the gap, tissue, or other anatomical features around the perimeter of and adjacent to, but not attached to or in intimate contact with, the heart 26 and not above the sternum or ribcage (e.g. within the pleural cavity). As such, leads 16 and 18 may be implanted anywhere within the "substernal location" defined by the undersurface between the sternum and/or ribcage and the body cavity but not including the pericardium or other portion of heart 26. The substernal location may alternatively be referred to by the terms "retrosternal space" or "mediastinum" or "infrasternal" as is known to those skilled in the art and includes the anterior mediastinum 36. The substernal location may also include the anatomical region described in Baudoin, Y. P., et al., entitled "The superior epigastric artery does not pass through Larrey's space (trigonum sternocostale)." Surg. Radiol. Anat. 25.3-4 (2003): 259-62 as Larrey's space. In other words, the distal portion of lead 16 may be implanted in the region around the outer surface of heart 26, but not attached to heart 26. Such leads may also be referred to herein as substernal leads, extra-pericardial and/or extracardiac leads.

The distal portion of leads 16 and 18 may be implanted within anterior mediastinum 36 such that electrode 24 is located proximate a ventricle of heart 26. For instance, leads 16 and 18 may be implanted within anterior mediastinum 36 such that electrodes 24 and 32 are located over a cardiac silhouette of one or both ventricles as observed via an anterior-posterior (AP) fluoroscopic view of heart 26. In one example, leads 16 and 18 may be implanted such that a therapy vector from electrodes 24 and 32 to a housing electrode of ICD 14 is substantially across the ventricles of heart 26. The therapy vector may be viewed as a line that extends from a point on electrode 24 (or 32), e.g., center of electrode 24 (or 32), to a point on the housing electrode of ICD 14, e.g., center of the housing electrode. However, leads 16 and 18 may be positioned at other locations as long as the therapy vector between electrodes 24 and 32 and the housing electrode is capable of defibrillating heart 26.

In the example illustrated in FIGS. 1A and 1B, leads 16 and 18 are located substantially under the sternum, extending substantially parallel to one another, and spaced apart from one another by a distance. The distance between electrode 24 of lead 16 and electrode 32 of lead 18 may be anywhere from 0-60 millimeters (mm). In one specific example, the distance between electrodes 24 of lead 16 and electrode 32 of lead 18 may be between approximately 10-40 mm and, more specifically between approximately 15-30 mm and, even more specifically between approximately 20-25 mm. The distance between the leads and/or the defibrillation electrodes of the leads may be dependent upon the whether designing for reduced defibrillation energy thresholds (DFTs), for reducing non-uniformity of the defibrillation field, for reducing load impedance, or other parameter.

Leads 16 and 18 could be implanted in a manner that provides for the distance of separation between the electrodes 24, 32 of leads 16, 18. For example, an implanter of leads 16, 18 could ensure the separation via fluoro. In other instances, the implant tool or one or both of leads 16, 18 may include some sort of feature to ensure the appropriate or desired distance of separation between the electrodes 24, 32 of leads 16, 18. For example, one or both of leads 16, 18 may include wings, tabs, thick-walled outer insulation or other feature to ensure a desired distance between the electrodes 24, 32 of leads 16, 18.

In other instances, however, leads 16 and 18 may be implanted such that one or both of leads 16 and 18 are offset laterally from the center of the sternum. In some instances, leads 16 and/or 18 may extend laterally enough such that all or a portion of leads 16 and/or 18 is underneath/below the ribcage in addition to or instead of under the sternum.

The elongated lead body of leads 16 or 18 may be formed from a non-conductive material shaped to form one or more lumens within which one or more elongated electrical conductors (not illustrated) extend from the connector at the proximal lead end to respective ones of electrodes 24, 28, 30 and 32 located along the distal portion of respective lead 16 or 18. The elongated lead body may have a generally uniform shape along the length of the lead body. In one example, the elongated lead body may have a generally tubular or cylindrical shape along the length of the lead body. The elongated lead body may have a diameter of between 3 and 9 French (Fr) in some instances. However, lead bodies of less than 3 Fr and more than 9 Fr may also be utilized. In another example, the distal portion (or all of) the elongated lead body may have a flat, ribbon or paddle shape. In this instance, the width across the flat portion of the flat, ribbon or paddle shape may be between 1 and 3.5 mm. Other lead body designs may be used without departing from the scope of this disclosure. The lead body of lead 16 may be formed from a non-conductive material, including silicone, polyurethane, fluoropolymers, or other appropriate materials, or mixtures thereof. However, the techniques of this application are not limited to such constructions.

The one or more elongated electrical conductors contained within the lead body of leads 16 or 18 may engage with respective ones of electrodes 24, 28, 30 and 32. In one example, each of electrodes 24, 28 and 30 is electrically coupled to a respective conductor within the lead body of lead 16. In some instances, more than one conductor may be coupled to a single electrode, as described in further detail in the discussion of series coupling of defibrillation electrodes. The respective conductors may electrically couple to circuitry, such as a therapy module and/or a sensing module, of ICD 14 via connections in connector assembly, including associated feedthroughs. The electrical conductors transmit therapy from the therapy module within ICD 14 to one or more of electrodes 24, 28, 30 and 32 and transmit sensed electrical signals from one or more of electrodes 24, 28, 30 and 32 to the sensing module within ICD 14.

Electrodes 24 and 32 are generally designed for use in delivering high voltage cardioversion/defibrillation therapy. As such, electrodes 24 and 32 are often referred to as high voltage electrodes or defibrillation electrodes. Defibrillation electrodes 24 and 32 may be elongated coil electrodes. Defibrillation electrodes 24 and 32 may vary in length depending on a number of variables. Defibrillation electrodes 24 and 32 may, in one example, have a length between approximately 5-10 centimeters (cm). However, defibrillation electrodes 24 and 32 may have a length less than 5 cm and greater than 10 cm in other embodiments. In another example, defibrillation electrodes 24 and 32 may have a length between approximately 2-16 cm. Defibrillation electrodes 24 and 32 may have the same or different lengths. For example, defibrillation electrode 32 may be longer than electrode 24 due to the fact that lead 18 includes fewer electrodes along the distal portion of the leady body. In addition to the distance between the leads and/or the electrodes, the length of the electrodes also may affect the DFT. In general, the longer the coil lengths the lower the DFTs.

In other embodiments, however, defibrillation electrodes 24 and/or 32 may be a flat ribbon electrode, paddle electrode, braided or woven electrode, mesh electrode, segmented electrode, directional electrode, patch electrode or other type of electrode besides an elongated coil electrode. In one example, defibrillation electrodes 24 and/or 32 may be formed of one or more segments separated by a distance, such as is described in U.S. patent application Ser. No. 14/519,436, entitled "IMPLANTABLE EXTRAVASCULAR ELECTRICAL STIMULATION LEAD HAVING IMPROVED SENSING AND PACING CAPABILITY," the contents of which are incorporated by reference herein in its entirety. Defibrillation electrodes 24 and 32 may be the same shape or type of electrode in some instances. In other instances, however, defibrillation electrodes 24 and 32 may have different shapes or be different types of electrodes.

Lead 16 also includes electrodes 28 and 30 located along the distal portion of lead 16 utilized for pacing and/or sensing. Thus, electrodes 28 and 30 may sometimes be referred to as pace/sense electrodes or low voltage electrodes since pacing stimulation is associated with voltages that are significantly smaller than defibrillation stimulation. In the example illustrated in FIGS. 1A-C, electrodes 28 and 30 are separated from one another by defibrillation electrode 24. In other examples, however, electrodes 28 and 30 may both be distal of defibrillation electrode 24 or both be proximal of defibrillation electrode 24. In instances in which defibrillation electrode 24 is a segmented electrode with two or more defibrillation electrode segments (e.g., as described in previously referenced U.S. patent application Ser. No. 14/519,436), one or both of electrodes 28 and 30 may be located between the two defibrillation electrode segments. Electrodes 28 and 30 may comprise ring electrodes, short coil electrodes, hemispherical electrodes, segmented electrodes, directional electrodes, or the like. Electrodes 28 and 30 of lead 16 may have substantially the same outer diameter as the lead body. In one example, electrodes 28 and 30 may have surface areas between 1.6-55 mm$^2$. Electrodes 28 and 30 may, in some instances, have relatively the same surface area or different surface areas. Depending on the configuration of lead 16, electrodes 28 and 30 may be spaced apart by the length of defibrillation electrode 24 plus some insulated length on each side of defibrillation electrode 24, e.g., approximately 2-16 cm between electrodes 28 and 30. In other instances, such as when electrodes 28 and 30 are both distal or proximal to electrode 24 or when electrodes 28 and/or 30 are between a segmented defibrillation electrode, the electrode spacing may be smaller, e.g., less than 2 cm or less the 1 cm. The example dimensions provided above are exemplary in nature and should not be considered limiting of the embodiments described herein. In other examples, lead 16 may include a single pace/sense electrode or more than two pace/sense electrodes. Although not illustrated in FIGS. 1A and 1B, lead 18 may also include one or more sensing/pacing electrodes similar to electrodes 28 and/or 30.

As will be described in further detail herein, ICD 14 is configured to obtain electrical signals sensed at the substernal location of the patient, e.g., using electrodes 28 and/or 30, and to deliver high voltage shocks, e.g., defibrillation and/or cardioversion shocks, from the substernal location to heart 26 using electrode 24 of lead 16, electrode 32 of lead 18, and the housing electrode of ICD 14. ICD 14 may deliver the high voltage shocks to heart 26 using an electrode vector in which electrode 24 of lead 16 and electrode 32 of lead 18 are concurrently used as a first, common polarity (e.g., anode (positive polarity) or cathode (negative polarity)) of the electrode vector and the housing electrode is the second, opposite polarity (cathode or anode, respectively) of the electrode vector. Utilizing both substernal defibrillation electrodes 24 and 32 concurrently as a common polarity of the electrode vector may result in a reduction in the shock impedance and a reduction in the defibrillation threshold (DFT) compared to extravascular ICD systems that include only a single extravascular lead. In some instances, as described below with respect to FIG. 3, ICD 14 may be configurable (automatically or manually) to deliver high voltage shocks using only one of electrodes 24 or 32 in conjunction with the housing electrode of ICD 14 or between electrodes 24 or 32 in addition to the electrode vector described above in which electrodes 24 and 32 are concurrently used at a first, common polarity.

The examples illustrated in FIGS. 1A and 1B are exemplary in nature and should not be considered limiting of the techniques described in this disclosure. For example, ICD 14, lead 16, and lead 18 may be implanted at other locations. In one other configuration, for example, lead 18 may be implanted extra-thoracically as described below with respect to FIGS. 2A-2C. In another configuration, ICD 14 may be implanted in an extra-thoracic pocket (e.g, subcutaneous or submuscular pocket) in the right pectoral region and leads 16 and 18 may extend extra-thoracicly from the device toward the manubrium of the sternum and bend or turn and extend substernally inferior from the manubrium to the desired location.

Figure 2A:
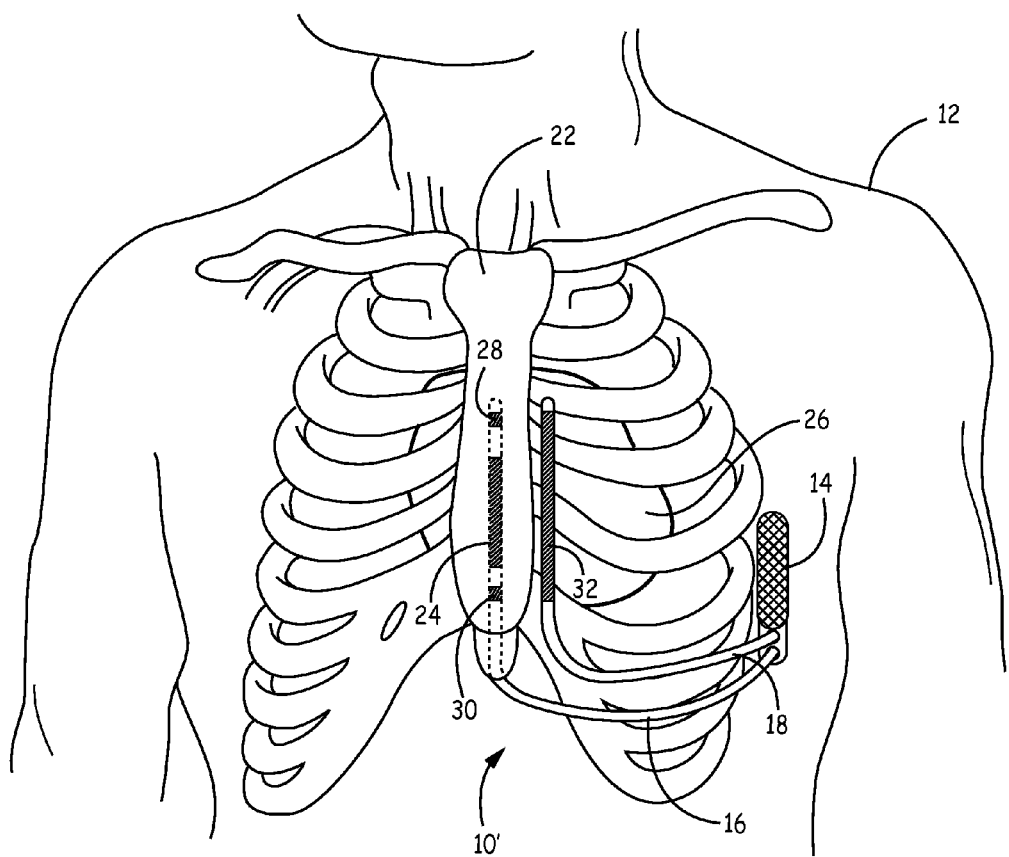
FIGS. 2A-C are conceptual diagrams of another example extravascular ICD system having two electrical stimulation leads, each with a respective defibrillation electrode, one of which is implanted within a substernal location of the patient and the other is implanted in an extra-thoracic location.
Figure 2B:
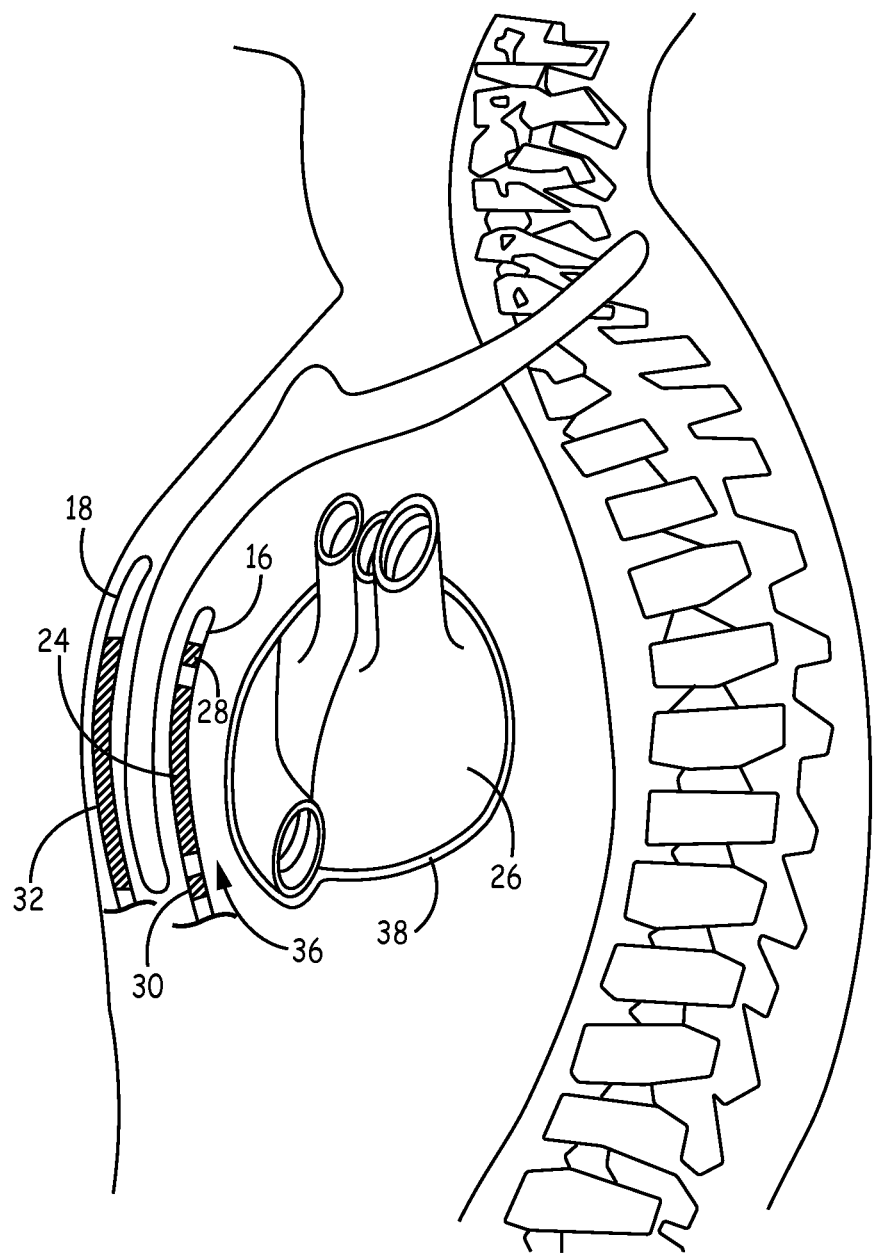
Figure 2C:
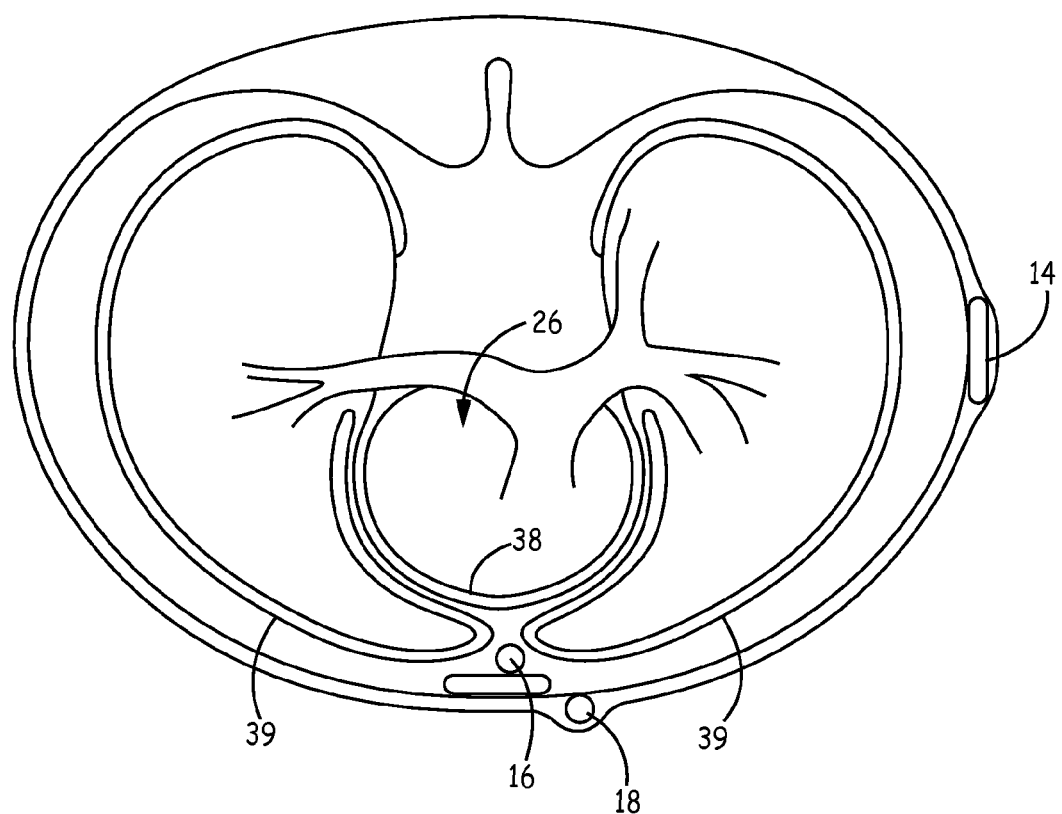

FIGS. 2A-C are conceptual diagrams of another example extravascular ICD system 10' implanted within a patient 12. FIG. 2A is a front view of patient 12 implanted with ICD system 10'. FIG. 2B is a side view of patient 12 with ICD system 10'. FIG. 2C is a transverse view of patient 12 implanted with ICD system 10'. Extravascular ICD system 10' conforms substantially with extravascular ICD system 10 of FIGS. 1A and 1B, except electrical stimulation lead 18 is implanted or positioned extra-thoracically (outside the ribcage and sternum, e.g., subcutaneously or submuscularly). Therefore, the complete description of the system will not be repeated, but only the differences will be described in detail.

In the example illustrated in FIGS. 2A-2C, lead 18 extends extra-thoracically outside of the ribcage from ICD 14 toward a center of the torso of patient 12, but unlike in system 10, lead 18 bends or turns and extends superior extra-thoracically outside of the ribcage and/or sternum, substantially parallel to the sternum instead of substernally as in FIGS. 1A and 1B. Leads 16 and 18 again extend substantially parallel to one another. As such, defibrillation electrode 32 is located extra-thoracically instead of substernally. Although illustrated in FIGS. 2A-2C as being offset laterally from and extending substantially parallel to the sternum, lead 18 may be implanted at other locations, such as over the sternum, offset to the right or left of the sternum, angled lateral from the sternum at either the proximal or distal end, implanted within the pleural cavity or the like.

As described in more detail below, ICD 14 is configured to obtain electrical signals sensed at the substernal location of the patient, e.g., using electrodes 28 and/or 30 and/or the housing electrode of ICD 14 (an possibly in conjunction with defibrillation electrodes 24, 32), and to deliver high voltage shocks, e.g., defibrillation and/or cardioversion shocks, to heart 26 using electrode 24 of lead 16, electrode 32 of lead 18, and/or the housing electrode of ICD 14. ICD 14 may deliver the high voltage shocks to heart 26 using an electrode vector in which electrode 24 of lead 16 and electrode 32 of lead 18 form or are at a first polarity of the electrode vector (e.g., are a common anode or cathode) and the housing electrode forms or is at a second polarity of electrode vector (e.g., is a cathode or anode). Utilizing both defibrillation electrodes 24 and 32 concurrently as a common polarity of the electrode vector (e.g., common anode or cathode) may result in a reduction in the shock impedance and a reduction in the defibrillation threshold (DFT) compared to extravascular ICD systems that include only a single extravascular lead.

Figure 3:
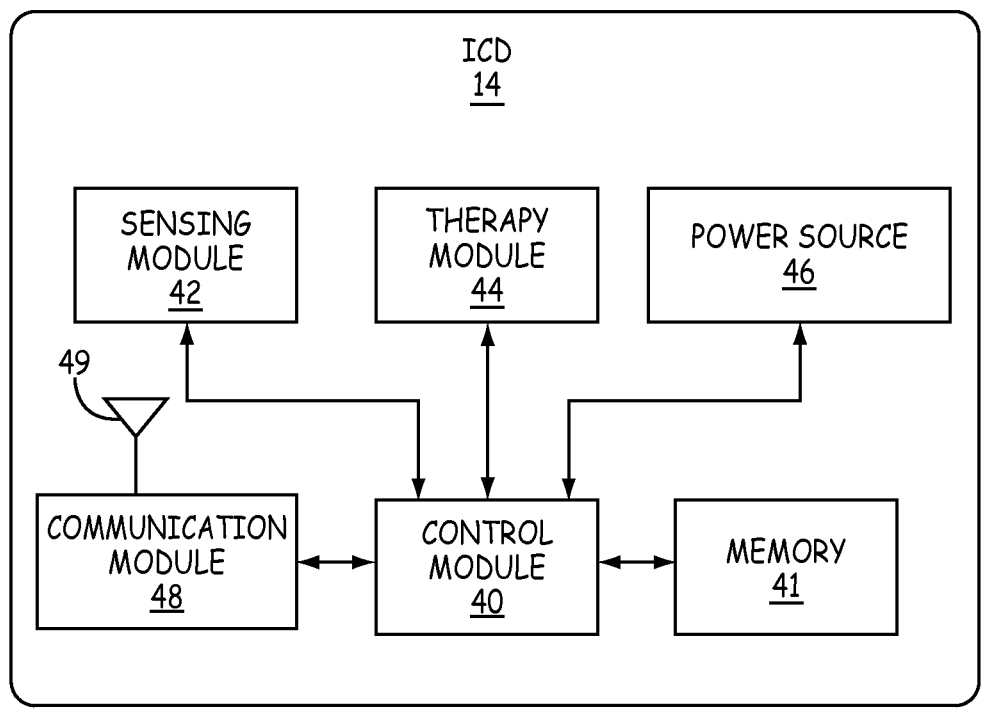
FIG. 3 is a functional block diagram of an example configuration of electronic components of an example ICD.

FIG. 3 is a functional block diagram of an example configuration of electronic components of an example ICD 14. ICD 14 includes a control module 40, sensing module 42, therapy module 44, communication module 48, and memory 41. The electronic components may receive power from a power source 46, which may, for example, be a rechargeable or non-rechargeable battery. In other embodiments, ICD 14 may include more or fewer electronic components. The described modules may be implemented together on a common hardware component or separately as discrete but interoperable hardware, firmware or software components. Depiction of different features as modules is intended to highlight different functional aspects and does not necessarily imply that such modules must be realized by separate hardware, firmware or software components. Rather, functionality associated with one or more modules may be performed by separate hardware, firmware or software components, or integrated within common or separate hardware, firmware or software components.

Sensing module 42 is electrically coupled to some or all of electrodes 24, 28, 30 and 32 via the conductors of leads 16 and 18 and one or more electrical feedthroughs, and is also electrically coupled to the housing electrode via conductors internal to the housing of ICD 14. Sensing module 42 is configured to obtain signals sensed via one or more combinations of electrodes 24, 28, 30 and 32, and the housing electrode of ICD 14 and process the obtained signals.

The components of sensing module 42 may be analog components, digital components or a combination thereof. Sensing module 42 may, for example, include one or more sense amplifiers, filters, rectifiers, threshold detectors, analog-to-digital converters (ADCs) or the like. Sensing module 42 may convert the sensed signals to digital form and provide the digital signals to control module 40 for processing or analysis. For example, sensing module 42 may amplify signals from the sensing electrodes and convert the amplified signals to multi-bit digital signals by an ADC. The digital signals output by sensing module 42 may include, for example, an electrogram (EGM) waveform. Sensing module 42 may also compare processed signals to a threshold to detect the existence of cardiac depolarizations, namely atrial or ventricular depolarizations (e.g., P- or R-waves), and indicate the existence of the atrial depolarization (e.g., P-waves) or ventricular depolarizations (e.g., R-waves) to control module 40.

Control module 40 processes the signals from sensing module 42 to monitor electrical activity of heart 26 of patient 12. Control module 40 may be a processor in one example. Control module 40 may store signals obtained from sensing module 42 as well as any generated EGM waveforms, marker channel data or other data derived based on the sensed signals in memory 41. Control module 40 also analyzes the EGM waveforms and/or marker channel data to detect cardiac events (e.g., tachyarrhythmia). Control module 40 may analyze the sensed electrical signals obtained from one or more of the sensing vectors of lead 16 to monitor for tachyarrhythmia, such as ventricular tachycardia (VT) or ventricular fibrillation (VF). Control module 40 may analyze the heart rate and/or morphology of the sensed electrical signals to monitor for tachyarrhythmia in accordance with any of a number of techniques known in the art. Examples of algorithms that may be performed by control module 40 for detecting, discriminating and treating shockable rhythms are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), U.S. Pat. No. 8,437,842 (Zhang, et al.), and U.S. Pat. Pub. No. 2015/0273227 (Zhang et al.). The entire content of all of these patents and patent applications are incorporated by reference herein in their entirety.

In response to detecting an abnormal arrhythmia (e.g., VT or VF), control module 40 may control ICD 14 to generate and deliver the desired electrical stimulation therapy (e.g., defibrillation or cardioversion shock(s), ATP, post-shock pacing, bradycardia pacing, or the like) according to one or more therapy programs, which may be stored in memory 41, to treat the abnormal arrhythmias. Therapy module 44 may include one or more pulse generators, capacitors, transformers, H-bridge, switches, transistors, diodes, and/or other components capable of generating and/or storing energy to deliver as pacing therapy, defibrillation therapy, cardioversion therapy, cardiac resynchronization therapy, other therapy or a combination of therapies. Control module 40 may, for example, selectively couple the circuitry of therapy module 44 to power source 46 to charge the capacitor(s) to a desired voltage and then selectively couple the capacitor(s) of therapy module 44 to combinations of electrodes 24, 28, 30 and 32 of leads 16 and 18, and the housing electrode of ICD 14. In some instances, therapy module 44 may include a first set of components configured to provide pacing therapy and a second set of components configured to provide defibrillation therapy. In other instances, the same set of components may be configurable to provide both pacing and defibrillation therapy. In still other instances, some of the defibrillation and pacing therapy components may be shared components while others are used solely for defibrillation or pacing.

Therapy module 44 delivers the generated electrical stimulation therapy to heart 26 via one or more combinations of electrodes 24, 28, 30 and 32 of leads 16 and 18, and the housing electrode of ICD 14. In the case of high voltage shocks, e.g., defibrillation or cardioversion shocks, control module 40 controls therapy module 44 to deliver the high voltage shocks to heart 26 using electrode 24 of lead 16, electrode 32 of lead 18, and/or the housing electrode of ICD 14. Control module 40 and/or therapy module 44 may, in one example, deliver the high voltage shock(s) to heart 26 using an electrode vector in which electrode 24 of lead 16 and electrode 32 of lead 18 form or are at a first polarity (e.g., a common anode or cathode) and the housing electrode forms or is at a second polarity (e.g., a cathode or anode).

In one example, therapy module 44 may include a single output that is concurrently coupled to electrode 24 of lead 16 and electrode 32 of lead 18 such that electrodes 24 and 32 function as or at a common polarity (a common anode or cathode) of the high voltage therapy electrode vector. In some instances, the respective conductors of electrode 24 of lead 16 and electrode 32 of lead 18 may be coupled to the single output of therapy module 44 in parallel. In other words, the proximal end of both coils could be connected to a common polarity output (e.g., anode or cathode) of high voltage circuitry of the therapy module 44 via one or more interconnects within the connector assembly, feedthrough, or printed circuit board. In other instances, the respective conductors of electrode 24 of lead 16 and electrode 32 of lead 18 may be coupled in series. In this case, the proximal end of electrode 24 of lead 16 may be connected to the distal end of electrode 32 of lead 18, which is connected to the output of high voltage circuitry of the therapy module 44. Alternatively, the proximal end of electrode 32 of lead 18 may be connected to the distal end of electrode 24 of lead 16, which is connected to the output of high voltage circuitry of the therapy module 44. To accomplish such a coupling, one of electrodes 24 and 32 (the first electrode in the series connection) may be coupled to two conductors (one coupled to the proximal end of the electrode and one coupled to the distal end of the electrode). The conductor coupled to the distal end of the electrode is then coupled to the conductor of the other one of electrodes 24 and 32 (the second electrode in the series connection). This may be accomplished in one embodiment using a coiled conductor that couples to the proximal portion of the electrode and a cable conductor that couples to a distal portion of the electrode.

In the examples described above in which the single output of the high voltage circuitry of the therapy module 44 is concurrently coupled to electrodes 24 and 32, the high voltage therapy current (or voltage) is distributed passively between electrodes 24 and 32, e.g., based on the relative impedances associated with electrodes 24 and 32. Such a configuration may result in both a reduction in the shock impedance and a reduction in the defibrillation threshold (DFT) compared to extravascular ICD systems that include only a single extravascular defibrillation electrode, e.g., a system including only a single defibrillation electrode located under the sternum. In one example, the shock (or load) impedance may be reduced by up to 10%, 20%, and even 30% compared to single coil substernal shock (or load) impedances. In another example, the DFT may be reduced by 20%, 30%, 40%, or even 50% compared to single coil substernal DFTs. Additionally, by distributing the shock current between electrode 24 and 32, there is a reduction in the possibility for electroporation heart damage from the substernal electrode 24.

In another example, the high voltage circuitry of therapy module 44 may include two high-voltage outputs of the same polarity (e.g. anode (positive) or cathode (negative)). In this case, one output is electrically connected to the conductor of electrode 24 of lead 16 and the second output of the same polarity is electrically connected to the conductor of electrode 32 of lead 18. Control module 40 and/or therapy module 44 may independently control each of the high voltage outputs to control the delivery of current to each of electrodes 24 and 32. For example, control module 40 and/or therapy module 44 may monitor the amount of current delivered to electrodes 24 and 32 to ensure that it does not exceed a predetermined limit.

In some instances, in addition to therapy module 44 delivering high voltage shocks using an electrode vector in which electrode 24 of lead 16 and electrode 32 of lead 18 form or are at a first polarity (e.g., a common anode or cathode) and the housing electrode forms or is at a second polarity (e.g., a cathode or anode), ICD 14 may be configurable (automatically or manually) to deliver high voltage shocks using only one of electrodes 24 or 32 in conjunction with the housing electrode of ICD 14 or between electrodes 24 or 32 (electrodes 24 and 32 have opposite polarity). In one example, control module 40 may select an electrode vector for delivering the high-voltage shocks, e.g., based on impedance.

Control module 40 controls therapy module 44 to generate electrical stimulation therapy with the amplitudes, pulse widths, timing, frequencies, or electrode combinations specified by the selected therapy program. In the case of high voltage therapy, e.g., defibrillation or cardioversion shocks provided by defibrillation electrode 24 of defibrillation lead 16, control module 40 controls therapy module 44 to generate defibrillation or cardioversion shocks having any of a number of waveform properties, including leading-edge voltage, tilt, delivered energy, pulse phases, and the like. Therapy module 44 may, for instance, generate monophasic, biphasic or multiphasic waveforms.

In addition to providing high voltage shock therapy, ICD 14 may be configured to provide pacing therapy, e.g., ATP, post-shock pacing, and/or bradycardia pacing via one or more of the electrodes. For example, control module 40 may control therapy module 44 to provide pacing therapy via electrodes 28, 30, and/or the housing electrode of ICD 14. In another example, control module 40 may control therapy module 44 to provide pacing therapy using defibrillation electrodes 24 and/or 32 (i.e., pacing between electrodes 24 and 32) or using one or both of defibrillation electrodes 24 and/or 32 in conjunction with one or more of electrodes 28, 30, or the housing electrode of ICD 14. Control module 40 controls therapy module 44 to generate and deliver pacing pulses with any of a number of amplitudes and pulse widths to capture heart 26. The pacing thresholds of heart 26 when delivering pacing pulses from the anterior mediastinum using lead 16 may depend upon a number of factors, including location, type, size, orientation, and/or spacing of electrodes 28 and 30, location of ICD 14 relative to electrodes 28 and 30, physical abnormalities of heart 26 (e.g., pericardial adhesions or myocardial infarctions), or other factor(s).

The increased distance from electrodes 28 and 30 of lead 16 to the heart tissue may result in heart 26 having increased pacing thresholds compared to transvenous pacing thresholds. To this end, therapy module 44 may be configured to generate and deliver pacing pulses having larger amplitudes and/or pulse widths than conventionally required to obtain capture via a transvenously implanted lead or a lead attached to heart 26. In one example, therapy module 44 may generate and deliver pacing pulses having amplitudes of less than or equal to 8 volts and pulse widths between 0.5-3.0 milliseconds. In another example, therapy module 44 may generate and deliver pacing pluses having amplitudes of between 5 and 10 volts and pulse widths between approximately 3.0 milliseconds and 10.0 milliseconds. In another example, therapy module 44 may generate and deliver pacing pluses having pulse widths between approximately 2.0 milliseconds and 8.0 milliseconds. In a further example, therapy module 44 may generate and deliver pacing pluses having pulse widths between approximately 0.5 milliseconds and 20.0 milliseconds. In another example, therapy module 44 may generate and deliver pacing pluses having pulse widths between approximately 1.5 milliseconds and 20.0 milliseconds.

In some cases, therapy module 44 may generate pacing pulses having longer pulse durations than conventional transvenous pacing pulses to achieve lower energy consumption. For example, therapy module 44 may be configured to generate and deliver pacing pulses having pulse widths or durations of greater than two (2) milliseconds. In another example, therapy module 44 may be configured to generate and deliver pacing pulses having pulse widths or durations of between greater than two (2) milliseconds and less than or equal to three (3) milliseconds. In another example, therapy module 44 may be configured to generate and deliver pacing pulses having pulse widths or durations of greater than or equal to three (3) milliseconds. In another example, therapy module 44 may be configured to generate and deliver pacing pulses having pulse widths or durations of greater than or equal to five (5) milliseconds. In another example, therapy module 44 may be configured to generate and deliver pacing pulses having pulse widths or durations of greater than or equal to ten (10) milliseconds. In a further example, therapy module 44 may be configured to generate and deliver pacing pulses having pulse widths between approximately 3-10 milliseconds. In a further example, therapy module 44 may be configured to generate and deliver pacing pulses having pulse widths or durations of greater than or equal to fifteen (15) milliseconds. In yet another example, therapy module 44 may be configured to generate and deliver pacing pulses having pulse widths or durations of greater than or equal to twenty (20) milliseconds.

Depending on the pulse widths, ICD 14 may be configured to deliver pacing pulses having pulse amplitudes less than or equal to twenty (20) volts, deliver pacing pulses having pulse amplitudes less than or equal to ten (10) volts, deliver pacing pulses having pulse amplitudes less than or equal to five (5) volts, deliver pacing pulses having pulse amplitudes less than or equal to two and one-half (2.5) volts, deliver pacing pulses having pulse amplitudes less than or equal to one (1) volt. In other examples, the pacing pulse amplitudes may be greater than 20 volts. Typically the lower amplitudes require longer pacing widths as illustrated in the experimental results. Reducing the amplitude of pacing pulses delivered by ICD 14 reduces the likelihood of extra-cardiac stimulation. Some experimental results are provided later illustrating some example combinations of pacing amplitudes and widths.

Communication module 48 includes any suitable hardware, firmware, software or any combination thereof for communicating with another device, such as a clinician programmer, a patient monitoring device, or the like. For example, communication module 48 may include appropriate modulation, demodulation, frequency conversion, filtering, and amplifier components for transmission and reception of data with the aid of antenna 49. Antenna 49 may be located within the connector block of ICD 14 or within housing ICD 14.

The various modules of ICD 14 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Memory 41 may include computer-readable instructions that, when executed by control module 40 or other component of ICD 14, cause one or more components of ICD 14 to perform various functions attributed to those components in this disclosure. Memory 41 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 4A:
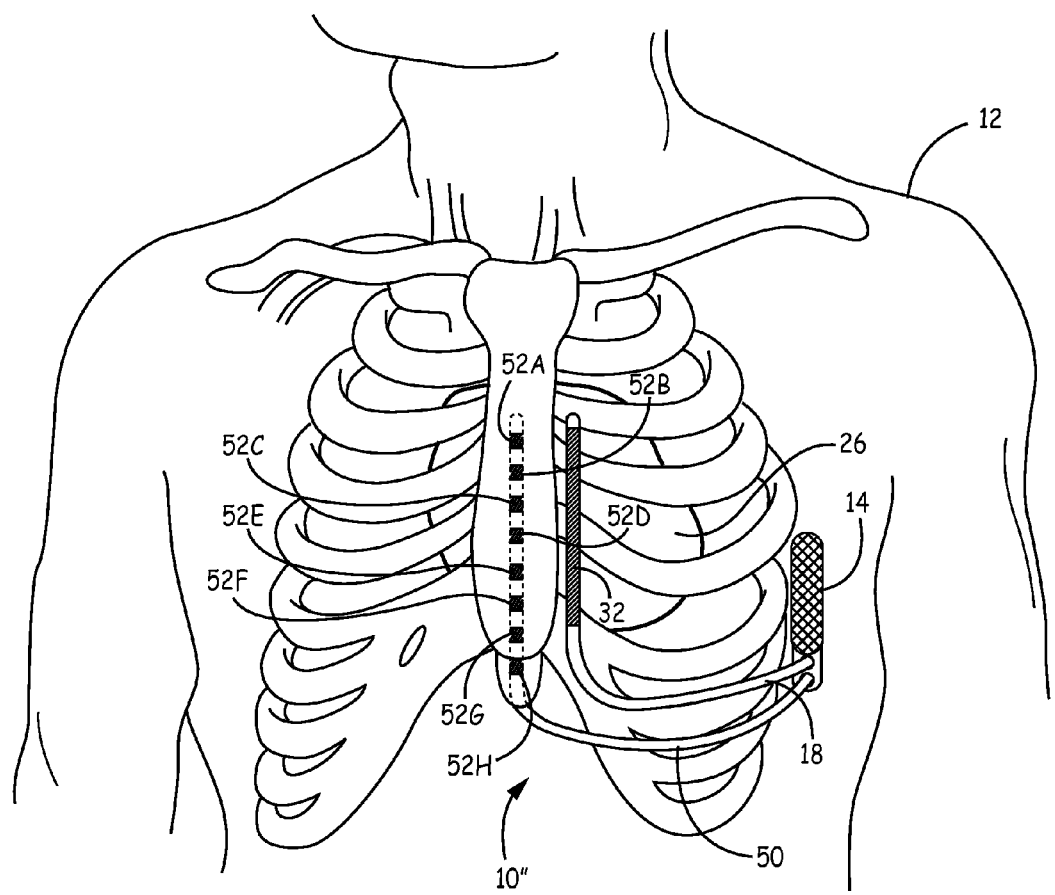
FIGS. 4A and 4B illustrates another example ICD system 10 in which one of the leads includes a plurality of discrete electrodes that collectively form the first defibrillation electrode.
Figure 4B:
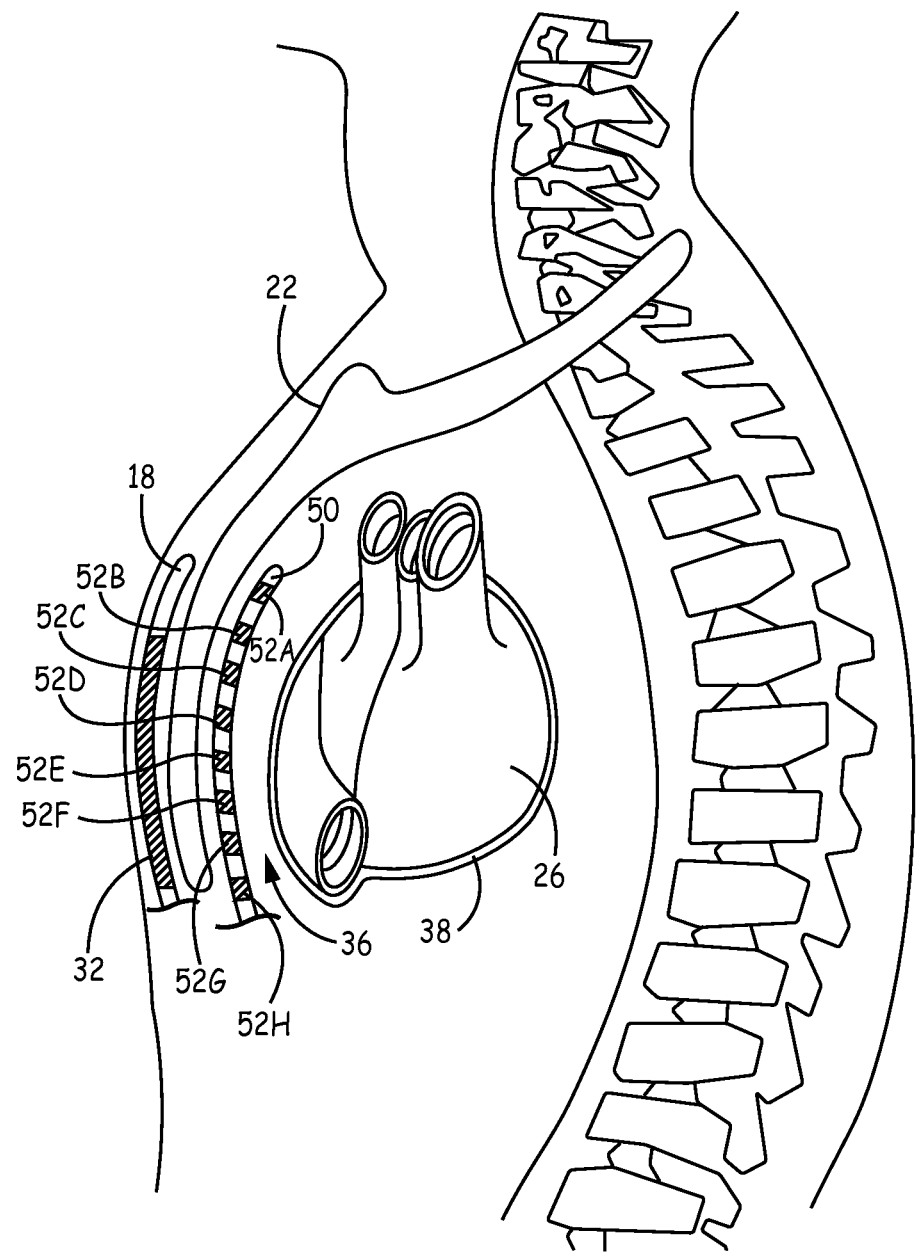

FIGS. 4A and 4B illustrates another example ICD system 10". ICD system 10" may include one or more of the structure and/or functionality of ICD system 10 of FIGS. 1A and 1B or ICD system 10' of FIGS. 2A-2C and ICD 14 of FIG. 3. Repetitive description of like numbered elements described in other embodiments is omitted for sake of brevity.

Lead 50 includes an elongated lead body, similar to the lead body of leads 16 or 18, having a proximal end that includes a connector (not shown) configured to be connected to ICD 14 and a distal portion that includes a plurality of electrodes 52A-52H. Like lead 16, lead 50 extends extrathoracically outside of the ribcage from ICD 14 toward a center of the torso of patient 12, e.g., toward the xiphoid process of patient 12. At a location near the center of the torso, lead 50 bends or turns and extends superior under the sternum and/or ribcage of patient 12. The distal portion of lead 50 may be implanted in similar locations to those described above with respect to lead 16.

A plurality of elongated electrical conductors contained within the lead body of lead 50 may engage with respective ones of electrodes 52. The plurality of electrical conductors electrically couple to circuitry, such as therapy module 44 and/or sensing module 42, of ICD 14 via connections in the connector assembly, including associated feedthroughs. The electrical conductors transmit therapy from therapy module 44 within ICD 14 to one or more of electrodes 52 and transmit sensed electrical signals from one or more of electrodes 52 to sensing module 42 within ICD 14.

In some instances, each of electrodes 52 is electrically coupled to a respective conductor within the lead body 54, e.g., electrodes 52 and the conductors have a 1:1 correspondence. In other instances, two or more electrodes 52 may be coupled to the same conductor within lead body 54. For example, lead 50 may include four electrical conductors within lead body 54 that each couple to pairs of electrodes 52, e.g., a first electrical conductor is coupled to electrodes 52A and 52H, a second electrical conductor is coupled to electrodes 52B and 52G, a third electrical conductor is coupled to electrodes 52C and 52F, and a fourth electrical conductor is coupled to electrodes 52D and 52E. However, the multiple conductors may be coupled to any combination of electrodes 52. As another example, electrode 52D may be coupled to a first conductor, electrode 52H may be coupled to a second conductor, electrodes 52E, 52F, and 52G may be coupled to a third conductor, and electrodes 52A, 52B, and 52C may be coupled to a fourth conductor. Also, there may be more or fewer electrodes 52.

Each of electrodes 52 may be a short coil electrode. In one example, each of the short coil segments forming electrodes 52 may be approximately equal to 1 centimeter (cm) in length. However, short coil electrodes 52 may be greater than or less than 1 cm in length. Short coil electrodes 52 may have the same lengths or different lengths. Short coil electrodes 52 may be spaced apart from one another. In one example, electrodes 52 may be spaced apart from one another by less than 1 cm, less than 0.5 cm, or less than 0.1 cm. However, other spacings and lengths greater than or less than those listed above may be used. Electrodes 52 may each be spaced apart from one another at equal distances or different distances. In other embodiments, electrodes 52 may be ring electrodes, paddle electrodes, hemispherical electrodes, directional electrodes, segmented electrodes, braided or woven electrodes, mesh electrodes or other type of electrode or combinations thereof. Additionally, although illustrated as including eight electrodes 52, lead 50 may include more or fewer electrodes.

As described above, ICD 14 obtains electrical signals sensed at the substernal location of the patient 12, e.g., using an electrode vector between two of electrodes 52 and/or between one or more of electrodes 52 and the housing electrode. In other instances, ICD 14 may be configured to obtain electrical signals sensed between one or more of electrodes 52 and defibrillation electrode 32 of lead 18. ICD 14 also delivers pacing pulses (e.g., ATP, post-shock pacing and/or bradycardia pacing) from the substernal location to the heart using an electrode vector between two or more of electrodes 52, between one or more of electrodes 52 and the housing electrode, between one or more of electrodes 52 and defibrillation electrode 32 of lead 18. As will be described further, ICD 14 may automatically select the electrode vector for pacing and/or sensing based on one or more characteristics of an EGM signal sensed using the electrode vector. For example, ICD 14 may automatically select the electrode vector for pacing and/or sensing based on one or more of an EGM amplitude, slew rate of the EGM or cardiac events in the EGM, stability of the EGM amplitude, stability of the EGM slew rate, impedance, segment motion and/or location relative to the heart, measured electrode polarization, or the like.

ICD 14 further delivers high voltage shocks (e.g., defibrillation and/or cardioversion shocks) to patient 12 using at least a portion of electrodes 52 of lead 50 in conjunction with electrode 32 of lead 18. In one example, ICD 14 may deliver high voltage shocks using all of the electrodes 52 of lead 50 and electrode 32 of lead 18. In another example, ICD 14 may deliver high voltage shocks using all of electrodes 52, except the most distal electrode 52A and the most proximal electrode 52H, in conjunction with electrode 32 of lead 18. Thus, ICD 14 may deliver the high voltage shocks using some or all of electrodes 52 and electrode 32 as a common polarity (anode or cathode) of the therapy electrode vector. A multi-segmented lead, such as lead 50, may provide a system that is less posture-dependent and/or lead-migration dependent by allowing multiple options for location of pacing therapy vectors while maintaining defibrillation performance by maintaining longer effective defibrillation electrode lengths.

Figure 5:
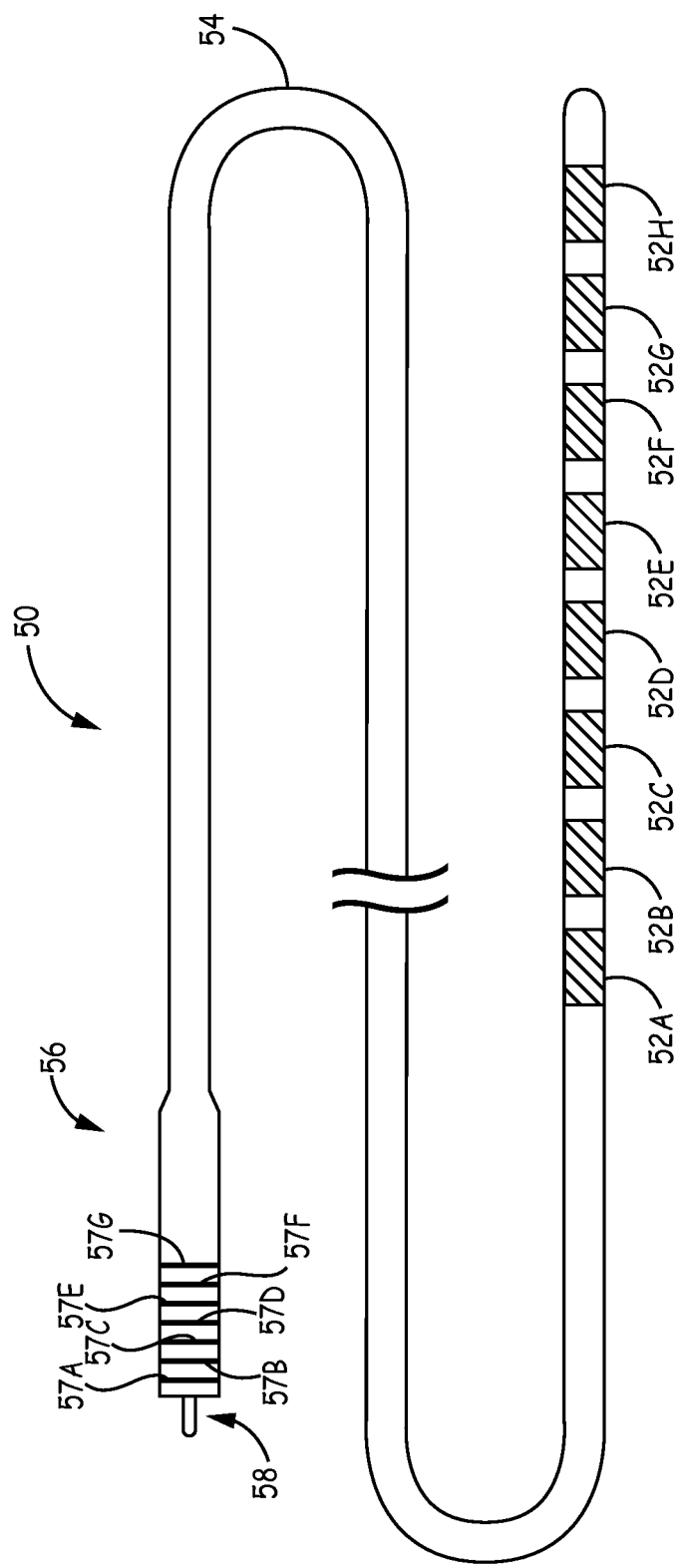
FIG. 5 illustrates the lead of FIGS. 4A and 4B in further detail.

FIG. 5 illustrates lead 50 of FIGS. 4A and 4B in further detail. As illustrated in FIG. 5, lead 50 includes a lead body 54 having a proximal end that includes a connector 56. Connector 56 includes a conductive pin 58 and a plurality of conductive rings 57A-57G that electrically connect each of the conductors within lead body 54 to the electronic components within ICD 14. In the example illustrated in FIG. 5, each of the electrodes 52 are coupled to a conductor within lead body 54, hence the eight electrical connections (pin 58+seven ring connections 57). As described above, however, there may be embodiments in which a single conductor within lead body 54 is electrically coupled to more than one of electrodes 52. In this case, there may be fewer electrical connections, e.g., rings 57, on connector 56.

Figure 6:
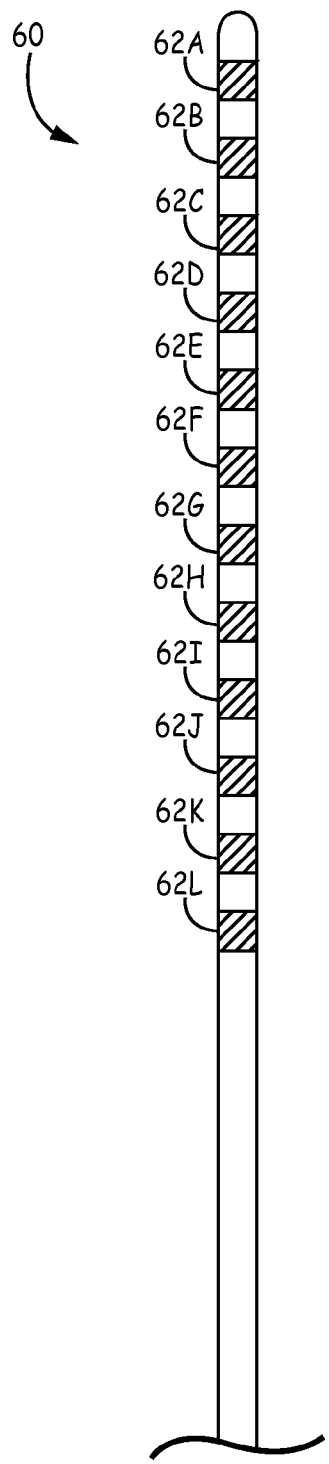
FIG. 6 illustrates a distal portion of another example lead having a plurality of discrete electrodes that collectively form the first defibrillation electrode.

FIG. 6 illustrates a distal portion of another example lead 60. Lead 60 can include one or more of the structure and/or functionality of lead 50 of FIGS. 4A, 4B and 5. For example, lead 60 may conform substantially to that of lead 50 except that lead 60 includes twelve ring electrodes 62A-62L instead of eight short coil electrodes 52. However, lead 60 may include more or fewer ring electrodes or a combination of ring and coil electrodes. Like electrodes 52 of lead 50, electrodes 62 of lead 60 may each be coupled to separate conductors extending within the lead body of lead 60. Alternatively, more than one of electrodes 62 may be electrically connected to a common conductor. Repetitive description of the structure and functionality of lead 50 will not be reproduced here for sake of brevity, but are equally applicable to lead 60.

Figure 7:
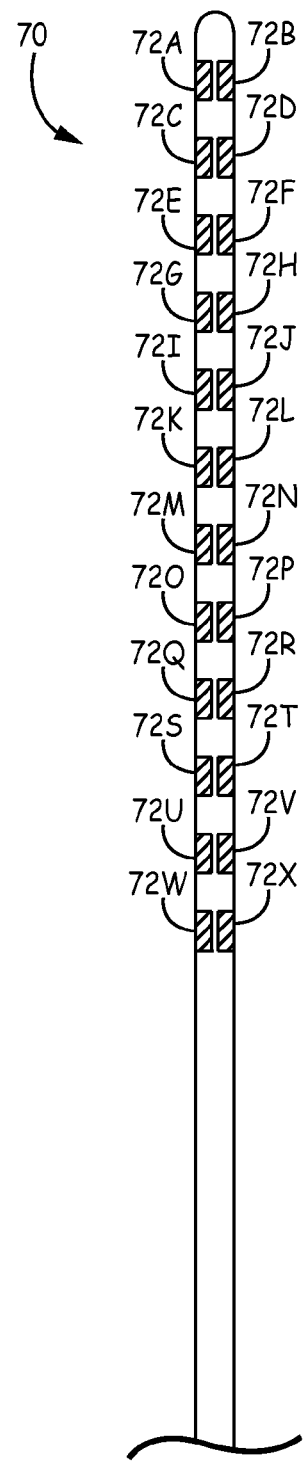
FIG. 7 illustrates a distal portion of another example lead having a plurality of discrete electrode segments that collectively form the first defibrillation electrode.

FIG. 7 illustrates a distal portion of another example lead 70. Lead 70 can include one or more of the structure and/or functionality of lead 50 of FIGS. 4A, 4B and 5 and/or lead 60 of FIG. 6. For example, lead 70 may conform substantially to that of lead 50 or 60 except that lead 70 includes segmented electrodes 72A-72X instead of short coil electrodes 52 or ring electrodes 62. Each of segmented electrodes 72 may extend around approximately half of the circumference of the lead body. In the example illustrated in FIG. 7, each segmented electrode 72 is arranged adjacent to another segmented electrode 72 such that two segmented electrodes (e.g., 72A and 72B) almost form a ring electrode, but include a small space between the two electrodes along the circumference of the lead body. In other embodiments, the segmented electrodes may not be arranged in pairs, but may instead by staggered along the distal portion of lead 70. Additionally, although electrodes 72 are illustrated as being segmented such that two electrodes extend around the circumference of the lead body, more than two electrode segments may exist around the circumference of the lead body. For example, electrodes 72 may by quarter-segments, such that there are four electrodes around the circumference of the lead body at a particular location along the length of the lead body.

Like electrodes 52 of lead 50 (or electrodes 62 of lead 60), electrodes 72 of lead 70 may each be coupled to separate conductors extending within the lead body of lead 70. Alternatively, more than one of electrodes 72 may be electrical connected to a common conductor. Repetitive description of the structure and functionality of lead 50 or lead 60 will not be reproduced here for sake of brevity, but are equally applicable to lead 70.

Figure 8:
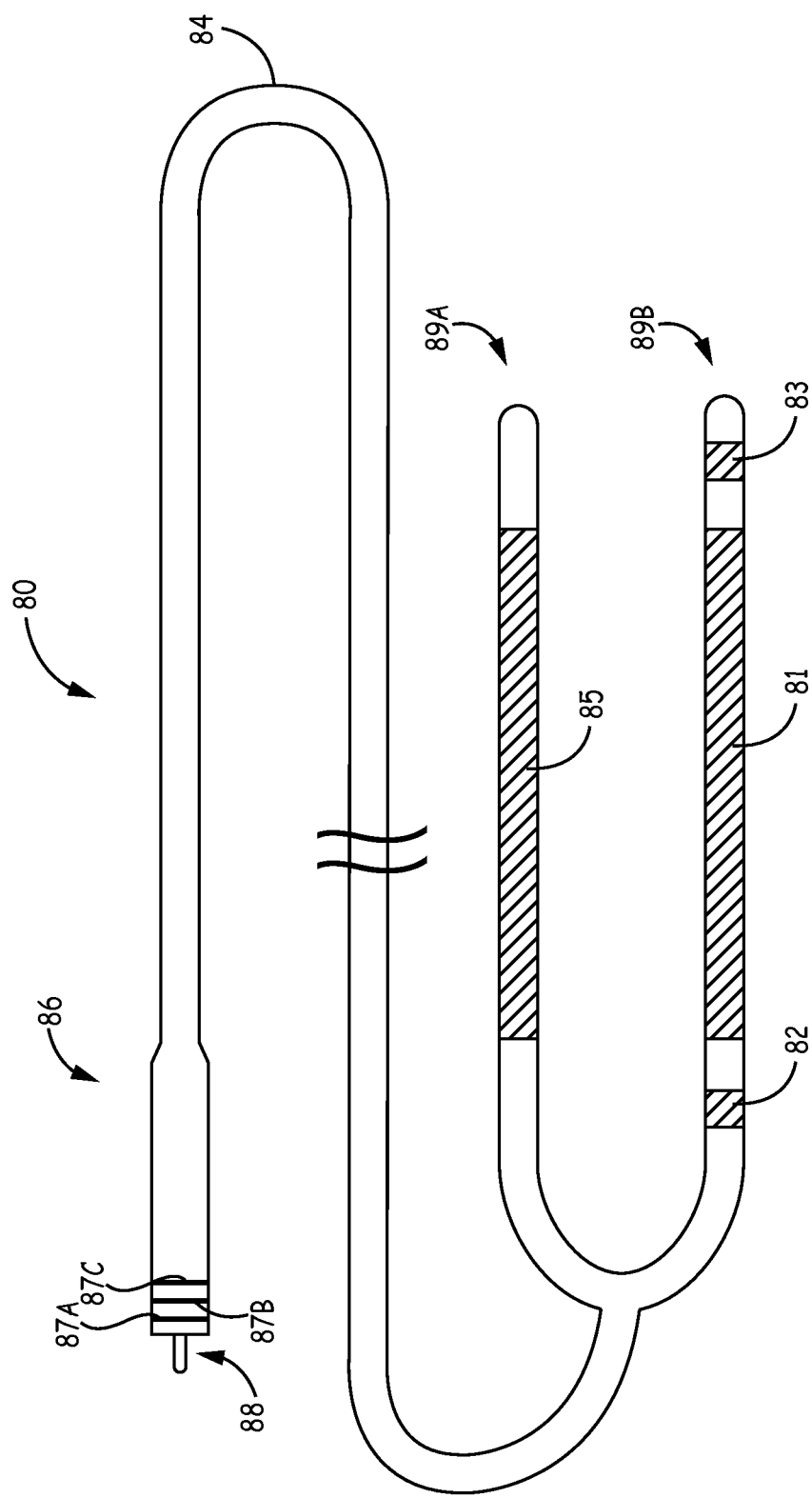
FIG. 8 illustrates an example electrical stimulation lead having a single connector on a proximal end and split lead segments at the distal portion having separate defibrillation electrodes.

FIG. 8 illustrates another example electrical stimulation lead 80. Lead 80 can include one or more of the structure and/or functionality of lead 50 of FIGS. 4A, 4B and 5, lead 60 of FIG. 6, and/or lead 70 of FIG. 7. Lead 80 includes a lead body 84 having a proximal end that includes a connector 86. Lead body 84 splits into two separate lead segments 89A and 89B at a distal end of lead body 84. Each of the lead segments 89 includes one or more electrodes. In the example illustrated in FIG. 8, lead segment 89A includes a defibrillation electrode 85 and lead segment 89B includes a defibrillation segment 81 and two pace/sense electrodes 81, 83.

Each of electrodes 81, 82, 83, and 85 are coupled to a conductor within lead body 84 and each of the conductors within the lead body is electrically coupled to one or more electrical connections of connector 86. In the example illustrated, connector 86 includes a conductive pin 88 and a plurality of conductive rings 87A-87C that electrically connect each of the conductors within lead body 84 to the electronic components within ICD 14. Thus, the four electrical connections (pin 88 and three ring connections 87) each electrical couple to a respective one of electrodes 81, 82, 83, and 85. In other examples, however, a single conductor within lead body 84 may be electrically coupled to more than one electrode, in which case there may be fewer electrical connections, e.g., fewer rings 87, on connector 86. In one particular alternative example, both defibrillation electrodes 81 and 85 may be coupled to a single conductor such that electrodes 81 and 85 have a common polarity when utilized to deliver defibrillation therapy to the heart of the patient. In the previous example in which the defibrillation electrodes 81 and 85 are coupled to separate conductors within lead body 84, defibrillation electrodes 81 and 85 may be coupled to a common polarity output of the therapy module 44 of ICD 14 using the techniques described herein.

Lead 80 may implanted such that both lead segment 89A and 89B are implanted in a substernal location. Alternatively, lead 80 may be implanted in a manner in which lead segment 89A is implanted extra-thoracically and lead segment 89B is implanted in a substernal location. In either case, lead 80 may be utilized to provide defibrillation therapy in accordance with the techniques described herein.

Figure 9:
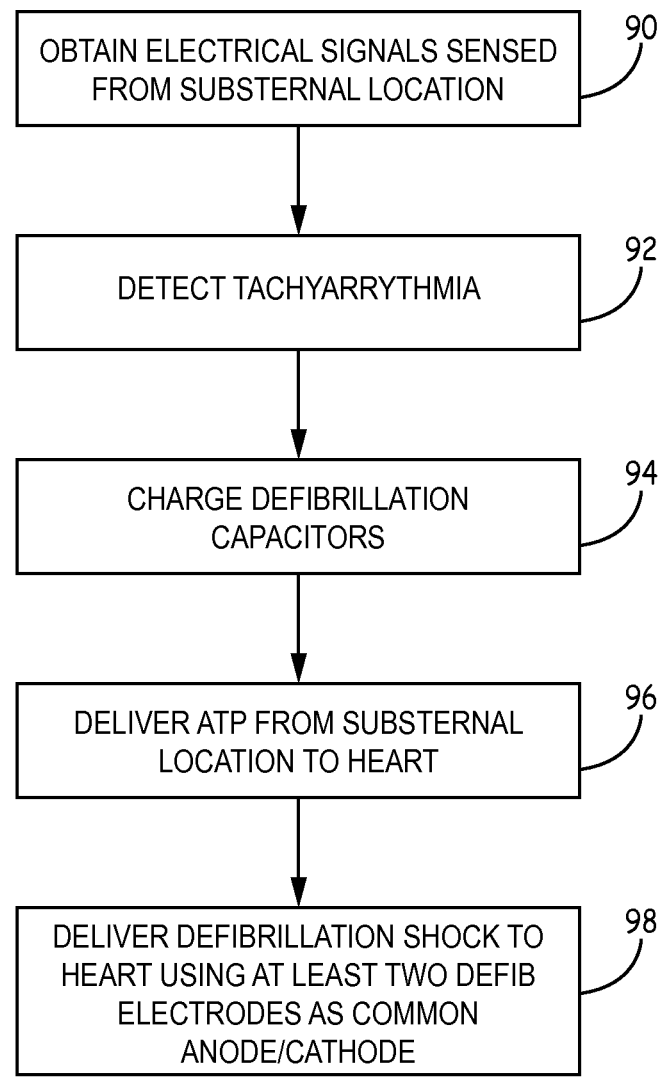
FIG. 9 illustrates a flow diagram illustrating exemplary operation of providing defibrillation in accordance with one aspect of this disclosure.

FIG. 9 illustrates a flow diagram illustrating exemplary operation of providing defibrillation in accordance with one aspect of this disclosure. Sensing module 42 obtains electrical signals sensed from the substernal location via one or more electrodes, such as electrodes 28, 30 and/or the housing electrode and/or electrodes 24, 32 (or electrodes 52, 62, or 72 in the case of leads 50, 60, or 70, respectively) (90). Control module 40 processes the signals from sensing module 42 to detect a tachyarrhythmia (e.g., VT or VF) (92). In response to detecting the tachyarrhythmia, control module 40 may control ICD 14 to generate and deliver the desired electrical stimulation therapy. Control module 40 controls therapy module 44 to charge one or more defibrillation capacitors (94). When the tachyarrhythmia is one that may be terminable using ATP (e.g., the tachyarrhythmia is VT), control module 40 may optionally control therapy module 44 to generate and deliver one or more sequences of ATP according to one or more therapy programs stored in memory 41 using electrodes 28, 30 and/or the housing electrode and/or electrodes 24, 32 (or electrodes 52, 62, or 72 in the case of leads 50, 60, or 70, respectively) (96). The ATP may be delivered during charging of the defibrillation capacitors, before charging, or after charging, or a combination thereof.

If the tachyarrhythmia is one that is not terminable using ATP (e.g., the tachyarrhythmia is VF) of if the ATP was unsuccessful in terminating the tachyarrhythmia, control module 40 may selectively couple the defibrillation capacitors of therapy module 44 to combinations of electrodes 24 and 32 of leads 16 and 18 as a common polarity of the electrode vector (anode or cathode) and the housing electrode of ICD 14 as the opposite polarity of the electrode vector (cathode or anode) (98). In instances in which one of leads 50, 60, or 70 are used, the common polarity of the electrode vector is formed using a plurality of electrodes 52, 62, or 72 and the defibrillation electrode 32.

Various examples of implantable medical systems and associated methods have been described for improving defibrillation therapies. One of ordinary skill in the art will appreciate that various modifications may be made to the described embodiments without departing from the scope of the following claims.

The invention claimed is:

1. An implantable cardioverter-defibrillator (ICD) system comprising:
   an ICD implanted in a patient under the skin and outside of the ribcage, the ICD including:
   a housing;
   a power source within the housing;
   a therapy module within the housing that includes at least one defibrillation capacitor; and
   a control module within the housing;
   a first electrical stimulation lead having a proximal portion coupled to the ICD and a distal portion having a first defibrillation electrode configured to deliver a defibrillation shock from a substernal location to a heart of the patient, the substernal location being at least partially within the anterior mediastinum; and
   a second electrical stimulation lead having a proximal portion coupled to the ICD and a distal portion having a second defibrillation electrode configured to deliver a defibrillation shock to the heart of the patient,
   wherein the control module is configured to couple the at least one defibrillation capacitor to an electrode vector to deliver a high voltage shock to the heart of the patient, wherein the control module couples the at least one defibrillation capacitor to the first and second defibrillation electrodes concurrently to form a first polarity of the electrode vector and to the housing of the ICD to form a second polarity of the electrical vector.

2. The ICD system of claim 1, wherein the second defibrillation electrode is configured to deliver the defibrillation shock from the substernal location to the heart of the patient.

3. The ICD system of claim 2, wherein one of the first defibrillation electrode includes a plurality of separate electrodes that collectively form the first defibrillation electrode.

4. The ICD system of claim 1, wherein
   the first electrical stimulation lead includes one or more electrodes separate from the first defibrillation electrode to sense electrical signals of the heart at the substernal location; and
   the ICD further includes a sensing module that obtains the sensed electrical signals of the heart sensed at the substernal location, wherein the control module analyzes the signals output from the sensing module to detect a tachyarrhythmia.

5. The ICD system of claim 1, wherein at least one of the first electrical stimulation lead and the second electrical stimulation lead includes one or more electrodes separate from the first and second defibrillation electrodes to deliver pacing pulses from the substernal location to the heart.

6. The ICD system of claim 1, wherein the control module is configured to couple the at least one defibrillation capacitor to the first defibrillation electrode and the second defibrillation electrode in parallel to form the first polarity of the electrode vector.

7. The ICD system of claim 6, wherein the therapy module includes a single high voltage output that electrically couples to the first defibrillation electrode and the second defibrillation electrode.

8. The ICD system of claim 6, wherein the therapy module includes a first high voltage output and a second high voltage output that are both associated with the first polarity, wherein the control module concurrently couples the first and second high voltage outputs to the first and the second defibrillation electrodes, respectively, to form the first polarity of the electrode vector.

9. The ICD system of claim 1, wherein the control module is configured to couple the at least one defibrillation capacitor to the first defibrillation electrode and the second defibrillation electrode in series to form the first polarity of the electrode vector.

10. The ICD system of claim 1, wherein the second defibrillation electrode is configured to deliver a defibrillation shock from the substernal location to the heart of the patient, the second defibrillation electrode being implanted in the substernal location.

11. The ICD system of claim 10, wherein the first electrical stimulation lead and the second electrical stimulation lead are separated from one another underneath the sternum by a distance.

12. The ICD system of claim 11, wherein the distance is between approximately 10-40 millimeters (mm).

13. The ICD system of claim 11, wherein the distance is between approximately 15-30 millimeters (mm).

14. The ICD system of claim 11, wherein the distance is between approximately 20-25 millimeters (mm).

15. The ICD system of claim 1, wherein the second defibrillation electrode is configured to deliver a defibrillation shock from an extra-thoracic location to the heart of the patient, the second defibrillation electrode being implanted extra-thoracically.

16. A method for extravascularly defibrillating a heart of a patient, the method comprising:
   obtaining electrical signals sensed from a substernal location via one or more electrodes in the substernal location;
   processing the electrical signals to detect a tachyarrhythmia;
   charging one or more defibrillation capacitors in response to detecting the tachyarrhythmia;
   electrically coupling the one or more defibrillation capacitors to an electrode vector to deliver a defibrillation therapy to the heart of the patient, the electrode vector including a first polarity formed by a first defibrillation electrode of a first electrical stimulation lead and a second defibrillation electrode of a second electrical stimulation lead and a second polarity formed by a housing of an implantable cardioverter-defibrillator (ICD), wherein the first defibrillation electrode is implanted at least partially in the substernal location.

17. The method of claim 16, further comprising delivering one or more sequences of anti-tachycardia pacing (ATP) pulses via the one or more electrodes in the substernal location.

18. The method of claim 16, wherein electrically coupling the one or more defibrillation capacitors to an electrode vector comprises electrically coupling the one or more defibrillation capacitors to the first defibrillation electrode and the second defibrillation electrode in parallel to form the first polarity of the electrode vector.

19. The method of claim 16, wherein electrically coupling the one or more defibrillation capacitors to an electrode vector comprises electrically coupling the one or more defibrillation capacitors to the first defibrillation electrode and the second defibrillation electrode in series to form the first polarity of the electrode vector.

20. The method of claim 16, wherein electrically coupling the one or more defibrillation capacitors to an electrode vector comprises electrically coupling a first high voltage output and a second high voltage output that are both associated with the first polarity, wherein the control module concurrently couples the first and second high voltage outputs to the first and the second defibrillation electrodes, respectively, to form the first polarity of the electrode vector.

21. An implantable cardioverter-defibrillator (ICD) system comprising:
   an ICD implanted in a patient under the skin and outside of the ribcage, the ICD including:
      a housing;
      a power source within the housing;
      a therapy module within the housing that includes at least one defibrillation capacitor; and
      a control module within the housing;
   an electrical stimulation lead having a lead body that includes a proximal portion configured to be coupled to the ICD and a distal portion that includes a first lead segment having a first defibrillation electrode configured to deliver a defibrillation shock from a substernal location to a heart of the patient, the first electrode being implanted at least partially along a posterior side of a sternum of the patient in the substernal location, and second lead segment having a second defibrillation electrode configured to deliver a defibrillation shock to the heart of the patient,
   wherein the control module is configured to couple the at least one defibrillation capacitor to an electrode vector to deliver a high voltage shock to the heart of the patient, wherein the control module couples the at least one defibrillation capacitor to the first and second defibrillation electrodes concurrently to form a first polarity of the electrode vector and to the housing of the ICD to form a second polarity of the electrical vector.

22. The ICD system of claim 21, wherein the control module is reconfigured to couple the at least one defibrillation capacitor to a second electrode vector to deliver a high voltage shock to the heart of the patient, wherein the control module couples the at least one defibrillation capacitor to the first defibrillation electrode to form a first polarity of the second electrode vector and to one of the housing of the ICD and the second defibrillation electrode to form a second polarity of the second electrical vector.

* * * * *